US010286090B2

(12) United States Patent
Jidong et al.

(10) Patent No.: US 10,286,090 B2
(45) Date of Patent: May 14, 2019

(54) TARGETED CONTRAST AGENTS COMPRISING A HYDRAZIDE FUNCTIONAL GROUP

(71) Applicant: RF Therapeutics Inc., Vancouver (CA)

(72) Inventors: Zhang Jidong, Ottawa (CA); Curry Ken, Richmond (CA)

(73) Assignee: RF Therapeutics Inc., Vancouver (CA)

( * ) Notice: Subject to any disclaimer, the term of this patent is extended or adjusted under 35 U.S.C. 154(b) by 11 days.

(21) Appl. No.: 15/534,352

(22) PCT Filed: Dec. 10, 2015

(86) PCT No.: PCT/CA2015/051304
§ 371 (c)(1),
(2) Date: Jun. 8, 2017

(87) PCT Pub. No.: WO2016/090491
PCT Pub. Date: Jun. 16, 2016

(65) Prior Publication Data
US 2017/0340757 A1 Nov. 30, 2017

Related U.S. Application Data

(60) Provisional application No. 62/090,519, filed on Dec. 11, 2014, provisional application No. 62/189,414, filed on Jul. 7, 2015.

(51) Int. Cl.
| | | |
|---|---|---|
| *A61K 49/10* | (2006.01) | |
| *A61K 49/08* | (2006.01) | |
| *C07D 403/12* | (2006.01) | |
| *C07D 403/14* | (2006.01) | |
| *C07D 257/02* | (2006.01) | |
| *C07C 243/38* | (2006.01) | |
| *C07D 209/42* | (2006.01) | |
| *C07D 249/04* | (2006.01) | |

(52) U.S. Cl.
CPC .......... *A61K 49/101* (2013.01); *A61K 49/085* (2013.01); *A61K 49/10* (2013.01); *A61K 49/108* (2013.01); *C07C 243/38* (2013.01); *C07D 209/42* (2013.01); *C07D 257/02* (2013.01); *C07D 403/12* (2013.01); *C07D 403/14* (2013.01); *C07D 249/04* (2013.01)

(58) Field of Classification Search
CPC ................................ A61K 49/08; A61K 49/10
See application file for complete search history.

(56) References Cited

U.S. PATENT DOCUMENTS

| 3,621,018 | A | 11/1971 | Hindersinn et al. |
| 5,679,810 | A | 10/1997 | Love et al. |
| 6,146,615 | A | 11/2000 | Davies et al. |
| 2001/0004454 | A1 | 6/2001 | Wedeking et al. |
| 2002/0076379 | A1 | 6/2002 | Platzek et al. |
| 2003/0171561 | A1 | 9/2003 | Pillai et al. |
| 2007/0122340 | A1 | 5/2007 | Yicheng et al. |

FOREIGN PATENT DOCUMENTS

| CA | 2814953 | A1 | 6/2012 |
| CN | 1486299 | A | 3/2004 |
| GB | 2368843 | A | 5/2002 |
| WO | 0009169 | A1 | 2/2000 |
| WO | 0238546 | A1 | 5/2002 |
| WO | 02059076 | A1 | 8/2002 |
| WO | 2012142702 | A1 | 10/2012 |
| WO | WO2012142702 | | * 10/2012 |

OTHER PUBLICATIONS

Chong et al., "Synthesis and Biological Evaluation of a Novel Decadentate Ligand DEPA," Bioorganic & Medicinal Chemistry Letters, Nov. 2008, vol. 18 (21), pp. 5792-5795.
International Patent Application No. PCT/CA2015/051304, International Search Report and Written Opinion dated Feb. 12, 2016.
International Patent Application No. PCT/CA2015/051304, International Preliminary Report on Patentability dated Jun. 22, 2017.
Jolley et al., "Improved synthesis and characterisation of a hydrazide derivative of diethylenetriaminepentaacetic acid for site-specific labelling of monoclonal antibodies with 111In", Applied Radiation and Isotopes, Jul. 1996, vol. 47 (7), pp. 623-626.
Martin et al., "Gadolinium (III) Di-and Tetrachelates Designed for in Vivo Noncovalent Complexation with Plasma Proteins: A Novel Molecular Design for Blood Pool MRI Contrast Enhancing Agents," Bioconjugate Chemistry, Sep. 1995, vol. 6 (5), pp. 616-623.
Mayor et al., "Synthesis of Vitamin B12 Derivatives with a Peripheral Metal Binding Site", Helvetica Chimica Act, Jun. 1997, vol. 80 (4), pp. 1183-1189.
Mishra et al., "A New Class of Gd-Based DO3A-Ethylamine-Derived Targeted Contrast Agents for MR and Optical Imaging," Bioconjugate Chemistry, Apr. 2006, vol. 17 (3), pp. 773-780.
Parac-Vogt et al., "Synthesis, Characterization, and Pharmacokinetic Evaluation of a Potential MRI Contrast Agent Containing Two Paramagnetic Centers with Albumin Binding Affinity," Chemistry: A European Journal, May 2005, vol. 11 (10), pp. 3077-3086.
Prinsen et al., "Development and Evaluation of a Ga-68 Labeled Pamoic Acid Derivative for in Vivo Visualization of Necrosis Using Positron Emission Tomography," Bioorganic & Medicinal Chemistry, Jul. 2010, vol. 18 (14), pp. 5274-5281.
Prinsen et al., "Radiolabeling and Preliminary Biological Evaluation of a (99M)Tc(C0)(3) Labeled 3,3 '-(Benzylidene)-Bis-(1H-indole-2-Carbohydrazide) Derivative as a Potential SPECT Tracer for in Vivo Visualization of Necrosis," Bioorganic & Medicinal Chemistry Letters, Oct. 2010, vol. 21 (1), pp. 502-505.

(Continued)

*Primary Examiner* — Michael G. Hartley
*Assistant Examiner* — Jagadishwar R Samala
(74) *Attorney, Agent, or Firm* — David Nauman; Borden Ladner Gervais LLP

(57) ABSTRACT

Described herein is a contrast agent for administration to a subject. The contrast agent includes a targeting portion that includes a hydrazide functional group; a metal ion bound to a metal-complexable portion; and a linker joining the targeting portion and the metal-complexable portion of the contrast agent. The portion that is not bound to a metal ion localizes the contrast agent to necrotic tissue in the subject.

11 Claims, 7 Drawing Sheets

(56) References Cited

OTHER PUBLICATIONS

European Patent Application No. 15866520.8, Extended European Search Report dated Jun. 19, 2018.

* cited by examiner

TARGETED CONTRAST AGENTS COMPRISING A HYDRAZIDE FUNCTIONAL GROUP

CROSS REFERENCE TO RELATED APPLICATIONS

This application claims the benefit of priority of U.S. Provisional Patent Application No. 62/090,519 filed Dec. 11, 2014, and U.S. Provisional Patent Application No. 62/189,414 filed Jul. 7, 2015, which are incorporated herein by reference in their entirety.

FIELD

The present disclosure relates generally to contrast agents and their methods of use.

BACKGROUND

Medical diagnostic imaging has evolved as an important non-invasive tool for medical diagnosis. Nuclear magnetic resonance imaging ("MRI") and computerized tomography ("CT") are two of the most widely used imaging methods. MRI generally relies on the relaxation properties of excited hydrogen nuclei in water. When the tissues or organs to be imaged are placed in a powerful, uniform magnetic field, the spins of the hydrogen protons within the tissues or organs align along the axis of the magnetic field. Medical imaging technologies also include ultrasound, SPECT or positron emission technology (PET) scans.

Imaging diagnosis plays an important role in medicine because it facilitates the accurate localization and characterization of disease that is critical for therapeutic decision-making and for the overall outcome of patient management. Due to technical innovations, imaging technologies have become much more powerful and versatile.

Although diagnostic imaging may be performed without the administration of contrast agents, the ability to improve the visualization of internal structures, for example tissues and organs, and fluids has resulted in the widespread use of contrast agents. Contrast agents are used to highlight specific areas to increase the visibility of the area being studied. Contrast agents for MRI technology alter the relaxation times of tissues and body cavities where they are located and work by shortening the relaxation time of protons located nearby.

The use of injectable contrast agents in conjunction with imaging techniques has increased dramatically over the last decade. These currently used contrast agents are generally safe, however, they are associated with some undesirable side effects. These side effects are divided into four major areas: systemic reactions, cardiac effects, renal effects, and general vascular effects. There have been many attempts to develop new contrast agents, with a primary aim of lessening the adverse effects.

Despite improvements in spatial and temporal resolution of diagnostic imaging, it remains difficult to make an unambiguous diagnosis even with the use of contrast agents. This problem may be attributed to the fact that there is substantial overlap in imaging signals between both pathological and normal tissues. One approach to solve this problem is to develop more specific contrast agents that specifically concentrate in targeted organs or tissues.

The use of porphyrins over the past decades sparked an interest in the development of new compounds that exhibit targeting capabilities. However, problems related to many porphyrin based contrast agents include instability, discoloration, toxicity and slow clearance rates. Several patent applications such as WO 00/09169 and WO 02/38546 discuss various non-porphyrin contrast agents that exhibit some "targeting" abilities however, problems related the reproducibility of these compounds along with slow clearance rates and longevity of the compound within the patient continue to exist.

It is, therefore, desirable to provide a contrast agent having more desirable pharmacokinetic related clearance properties and minimized toxicity and/or side-effects.

SUMMARY

It is an object of the present disclosure to obviate or mitigate at least one disadvantage of previous contrast agents.

In a first aspect, the present disclosure is based, in part, on the unexpected discovery that a targeting portion including an hydrazide functional group is able to target necrotic tissue.

The present disclosure provides a class of contrast agents comprising a targeting portion including a hydrazide functional group, a metal ion bound to a metal-complexable portion, and a linker joining the targeting portion and the metal-complexable portion of the contrast agent. The hydrazide functional group, on administration of the chelating agent to a subject, localizes in necrotic tissue.

In some embodiments, the metal complexable portion of the contrast agent includes an aminocarboxylate functional group.

In some embodiments, the aminocarboxylate functional group of the contrast agent is a polyaminocarboxylate functional group.

In some embodiments, there is provided a contrast agent comprising the structure X-L-Y*M, wherein X is the targeting portion, L is the linker, and Y*M is the metal ion (M) bound to the metal-complexable portion (Y) of the contrast agent, where X includes a hydrazide functional group.

In some embodiments, the contrast agents of the present disclosure are useful as therapeutic agents and/or diagnostic agents.

In some embodiments, the contrast agents of the present disclosure may be useful in medical applications involving necrosis and necrosis-related pathologies.

In some embodiments, the contrast agents of the present disclosure are useful for the manufacture of compositions and/or medicaments suitable for use in diagnostic imaging or imaging-aided applications, including for example MRI, CT, SPECT, PET, MRI-aided applications, CT-aided applications, SPECT-aided applications, or PET-aided applications.

In some embodiments, the contrast agents of the present disclosure are provided in combination with pharmaceutically acceptable carriers.

In some embodiments, the contrast agents of the present disclosure may be useful to monitor the effectiveness of an ongoing therapeutic treatment.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

FIG. 4 is a graphical representation of the results in FIGS. 1, 2 and 3.

DETAILED DESCRIPTION

Figure 1:
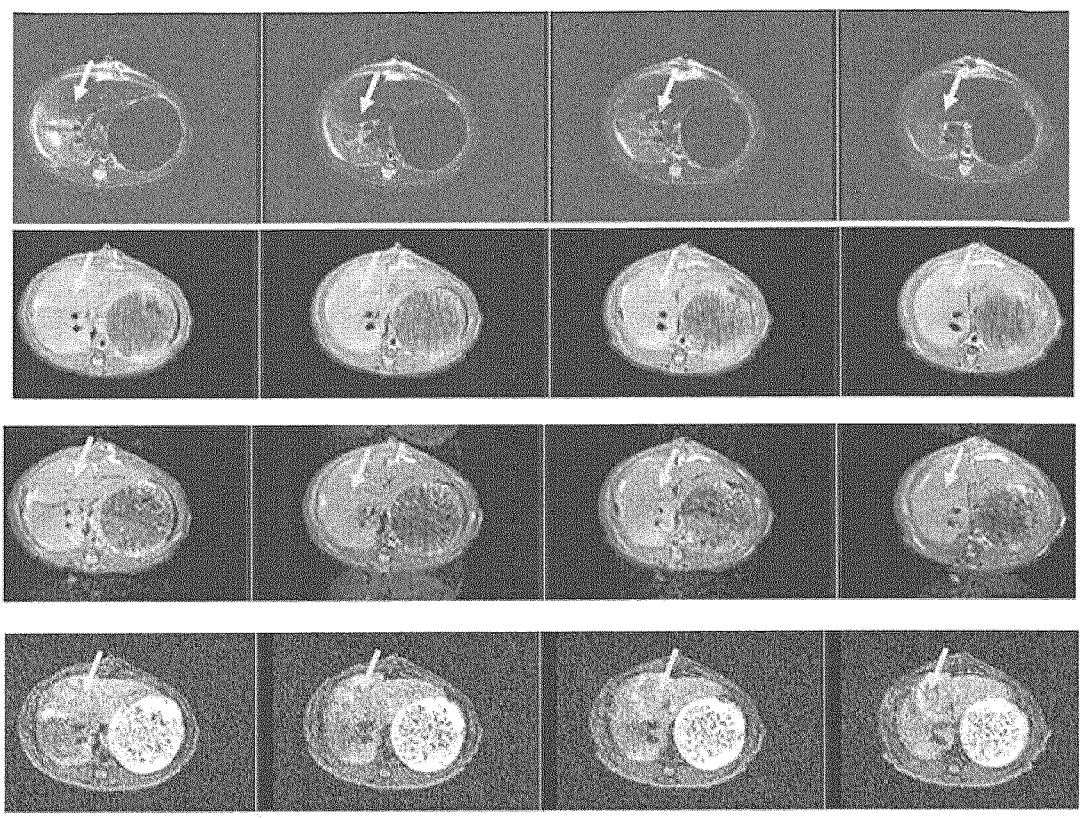
FIG. 1 shows magnetic resonance images of rat liver prior to administration of contrast agent RF1311.

Generally, the present disclosure provides contrast agents comprising, a targeting portion including a hydrazide functional group, a metal ion bound to a metal-complexable portion, and a linker joining the targeting portion and the metal-complexable portion of the contrast agent. The targeting portion localizes to necrotic tissue.

Traditional contrast agents have chemical structures where a single chelating agent is bound to a metal ion to form a complex such as Magnevist® (Gd-DTPA), Dotarem® (Gd-DOTA), Omniscan® (Gd-DTPA-BMA) and Pro-Hance® (Gd-HPDO3A). None of these traditional agents target specific organs or tissue of interest and often they are associated with unfavorable pharmacokinetics. These types of non-specific traditional agents typically have a very short half-life in plasma and a short time window for contrast-enhanced imaging which make it difficult to estimate the optimal imaging timing.

As used herein, the term 'subject' refers to an animal, such as a bird or a mammal. Specific animals include rat, mouse, dog, cat, cow, sheep, horse, pig or primate. A subject may further be a human, alternatively referred to as a patient. A subject may further be a transgenic animal. A subject may further be a rodent, such as a mouse or a rat.

Chelation is commonly applied in many areas, for example metal complex chemistry, organic and inorganic chemistry, and biochemistry. Chelating agents are used to control metal ions in aqueous systems, thus their popularity in the area of contrast agents in binding metal ions for use in diagnostic imaging. Chelating agents form stable water soluble complexes with multivalent metal ions and prevent undesired interaction by blocking normal reactivity of metal ions. Contrast agents of the present disclosure are T1 relaxation agents comprising a metal ion that is bound into a chelate complex. The MRI signal intensity relates to the value of the relaxation rate of tissues.

In general, the relaxation efficiency of a T1 contrast agent depends on several factors, including the nature of the metal ion and size and structure of the metal-chelate complex. T1 relaxation agents act as a relaxation sink for water protons. Paramagnetic metal chelates, for example, Gd(III), Fe(III), and Mn(II) complexes, may alter the relaxation rate of the surrounding water protons to allow for more effective MRI contrast enhancement. Chelate molecules are relatively large and have many bonds with the metal ion. There is a limited amount of free space within layer of atoms surrounding the metal ion, known as the coordination sphere. This lack of free space generally prevents the protons of the larger chelate molecule from getting sufficiently close to the metal ion for efficient energy transfer. As a result the tissue water is able to diffuse into the coordination sphere of the metal ion and give up its energy, and then exchange with the tissue water in turn enabling additional water molecules to enter the coordination sphere. The diffusion exchange occurs very quickly and the result is that the tissue water near the contrast agent has a larger net magnetization than the water in the neighboring tissue and contributes a stronger signal in a T1-weighted image.

The surprising discovery of the ability of a targeting portion including a hydrazide functional group to target and localize to necrotic tissue has led to the development of the contrast agents disclosed herein.

These contrast agents comprise: a targeting portion including a hydrazide functional group, a metal ion bound to a metal-complexable portion, and a linker joining the targeting portion and the metal-complexable portion. A person of skill in the art would understand a metal ion bound to a metal-complexable portion may also be referred to as a metal chelate. The targeting portion localizes the contrast agent to necrotic tissue following administration of the contrast agent to a subject.

In some embodiments, the contrast agents may be represented by the formula: X-L-Y*M, where X is the targeting portion, L is the linker, and Y*M is the metal ion (M) bound to the metal-complexable portion (Y). The targeting portion X includes a hydrazide functional group.

In some embodiments, the contrast agents may be represented by the formula: X-L-(Y*M)$_2$, where X is the targeting portion and includes a hydrazide functional group, L is the linker, and (Y*M)$_2$ represents two metal ions (M) bound to two metal-complexable portions (Y). As illustrated by this formula, there are two metal ions bound to the contrast agent and the metal ion and the contrast agent are in a 2:1 molar ratio. Contrast agents having (Y*M)$_n$ where n is 2, 3, 4 or 5 are also contemplated where the targeting portion is free to localize the contrast agent to necrotic tissue following administration of the contrast agent to a subject.

In some embodiments, the targeting portion may include a plurality of hydrazide functional groups. For example, the targeting portion may include 2, 3, 4, 5, 6, or 7 hydrazide functional groups. The hydrazide functional groups do not need to be directly bonded to a common portion of the contrast agent. Rather, a contrast agent may include a single metal-complexable portion bonded to a plurality of linkers, where each linker is bonded to a chemical group that includes a hydrazide functional group. In such a contrast agent, the targeting portion would be understood to include the plurality of chemical groups that include hydrazide functional groups.

In some embodiments, the metal complexable portion may be an aminocarboxylate functional group. In one aspect, the aminocarboxylate functional group may be a polyaminocarboxylate functional group.

Definitions

The term "linker" as used herein denotes a bond or chemical group that joins two or more other chemical groups. For example, in joining chemical groups R and R', a linker may be a bond that links R and R' directly, or may be a chemical group that is linked to R and R' via, for example, amide, ester, ether, hydrazide, nitrogen, or sulfur functionalities.

The linker may be alkyl, heteroalkyl, alkoxy, alkoxyalkyl, acyl, cycloalkyl, cycloalkylalkyl, aryl, heteroaryl, heterocycloalkyl, hydroxyalkyl, alkylthio, alkylcarbonylamino, alkylsulfinyl, alkylsulfonyl, alkylsulfonylamino, or heteroalkoxy. Preferably, the linker is an alkyl, aryl, heteroalkyl or heteroaryl linker.

The two ends of a compound that results in the linker group are preferably hydrazides. This allows the dihydrazide compound to be reacted with an acid or ester of a metal-complexable compound, thereby generating the contrast agent with a targeting portion that includes a hydrazide linked to a metal-complexable portion.

Examples of linker groups include, but are not limited to, R—R', R—C$_6$H$_4$—R', and R—CH$_2$CH$_2$—R', where R and R' represent the two chemical groups being linked together.

Other examples of linker groups include:

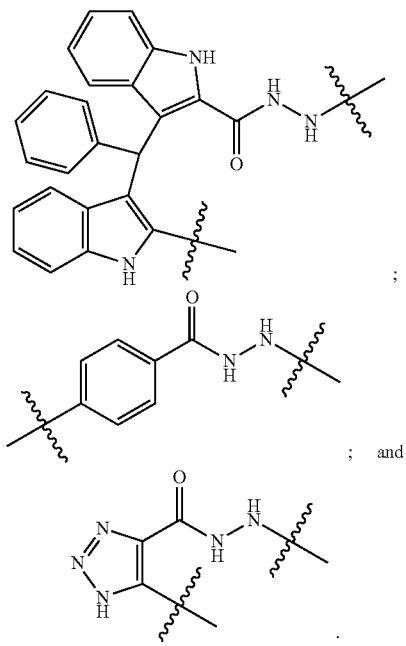

For example, the compound X-L-Y*M when L is a bond may be the product of the condensation of oxalyldihydrazide with an ester of a metal-complexable compound, such as 1,4,7,10-tetraazacyclododecane-1,4,7,10-tetraacetic acid (DOTA).

The term "metal-complexable portion" as used herein denotes a chemical group having ligands that can bond to a central metal atom to form a chelate complex. When acting as a magnetic resonance imaging (MRI) contrast agent, the chelate complex provides the metal with a coordination site to coordinate with a water molecule. The relaxation time of the complexed water molecule is altered and can be more readily discerned in an MRI image Specific examples of metal-complexable portion include:

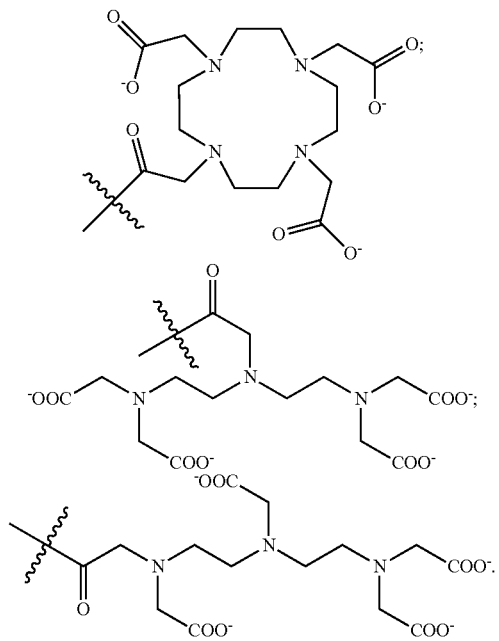

1,4,7,10-tetraazacyclododecane-1,4,7,10-tetraacetic acid (DOTA) and diethylene triamine pentaacetic acid (DTPA) are examples of metal-complexable portions that are particularly preferred.

The term "alkyl" as used herein denotes an unbranched or branched chain, saturated, hydrocarbon residue containing 1 to 20 carbon atoms. The term "lower alkyl" denotes a straight or branched chain hydrocarbon residue containing 1 to 10 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

"Heteroalkyl" means an alkyl moiety as defined herein, including a branched alkyl, which includes one or more heteroatoms. Exemplary heteroalkyl moieties can have one, two or three hydrogen atoms be replaced with a substituent independently selected from the group consisting of —OR$^a$, —NR$^b$R$^c$, and —S(O)$_n$R$^d$ (where n is an integer from 0 to 2), wherein R$^a$ is hydrogen, acyl, alkyl, cycloalkyl, or cycloalkylalkyl; R$^b$ and R$^c$ are independently of each other hydrogen, acyl, alkyl, cycloalkyl, or cycloalkylalkyl; and when n is 0, $R^d$ is hydrogen, alkyl, cycloalkyl, or cycloalkylalkyl; when n is 1, $R^d$ is alkyl, cycloalkyl, or cycloalkylalkyl; and when n is 2, $R^d$ is alkyl, cycloalkyl, cycloalkylalkyl, amino, acylamino, monoalkylamino, or dialkylamino. Other heteroalkyl moieties can have one or more heteroatoms inserted between carbon atoms. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylamino-sulfonylethyl, methylaminosulfonylpropyl, methylethylether, dimethylamine, adipic acid dihydrazide, and the like.

The term "alkylene" as used herein denotes a divalent saturated linear hydrocarbon radical of 1 to 20 carbon atoms (e.g., $(CH_2)_n$) or a branched saturated divalent hydrocarbon radical of 2 to 20 carbon atoms (e.g., —CHMe- or —$CH_2CH(i-Pr)CH_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The term "alkoxyalkyl" as used herein refers to the radical R'R"—, wherein R' is an alkoxy radical as defined herein, and R" is an alkylene radical as defined herein with the understanding that the attachment point of the alkoxyalkyl moiety will be on the alkylene radical. $C_{1-6}$ alkoxyalkyl denotes a group wherein the alkyl portion is comprised of 1-6 carbon atoms exclusive of carbon atoms in the alkoxy portion of the group. $C_{1-3}$ alkoxy-$C_{1-6}$ alkyl denotes a group wherein the alkyl portion is comprised of 1-6 carbon atoms and the alkoxy group is 1-3 carbons. Examples are methoxymethyl, methoxyethyl, methoxypropyl, ethoxymethyl, ethoxyethyl, ethoxypropyl, propyloxypropyl, methoxybutyl, ethoxybutyl, propyloxybutyl, butyloxybutyl, t-butyloxybutyl, methoxypentyl, ethoxypentyl, propyloxypentyl including their isomers.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl refers to a group —C(=O)R contain 6 carbon atoms. The term "arylcarbonyl" as used herein means a group of formula C(=O)R wherein R is an aryl group; the term "benzoyl" as used herein an "arylcarbonyl" group wherein R is phenyl.

"Cycloalkyl" means a saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkyl-amino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkylalkyl" mean a moiety of the formula —$R^a$—$R^b$, where $R^a$ is alkylene and $R^b$ is cycloalkyl as defined herein.

"Aryl" means a cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

The term "heteroaryl" or "heteroaromatic" as used herein means a monocyclic, bicyclic or tricyclic radical having at least one aromatic ring containing four to eight atoms per ring, incorporating one or more N, O, or S heteroatoms, the remaining ring atoms being carbon, with the understanding that the attachment point of the heteroaryl radical will be on an aromatic ring. As well known to those skilled in the art, heteroaryl rings have less aromatic character than their all-carbon counter parts. Thus, for the purposes of the application, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, pyrrolyl, pyrazolyl, imidazolyl, oxazol, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole and benzisothiazole. Bicyclic moieties can be optionally substituted on either ring; however the point of attachment is on a ring containing a heteroatom.

The term "heterocyclyl", "heterocycle", or "heterocycloalkyl" as used herein denotes a saturated cyclic radical, consisting of one or more rings, preferably one to two rings, of three to eight atoms per ring, incorporating one or more ring heteroatoms (chosen from N, O or $S(O)_{0-2}$), and which can optionally be independently substituted with one or more, preferably one or two substituents selected from hydroxy, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, unless otherwise indicated. Examples of heterocyclic radicals include, but are not limited to, azetidinyl, pyrrolidinyl, hexahydroazepinyl, oxetanyl, tetrahydrofuranyl, tetrahydrothiophenyl, oxazolidinyl, thiazolidinyl, isoxazolidinyl, morpholinyl, piperazinyl, piperidinyl, tetrahydropyranyl, thiomorpholinyl, quinuclidinyl and imidazolinyl. Preferably "heterocyclyl", "heterocycle", or "heterocycloalkyl" is a morpholinyl, pyrrolidinyl, piperidinyl or tetrahydrofuranyl.

The term "hydroxyalkyl" as used herein denotes an alkyl radical as herein defined wherein one to three hydrogen atoms on different carbon atoms is/are replaced by hydroxyl groups.

The term "alkylthio" or "alkylsulfanyl" refers to an —S-alkyl group, wherein alkyl is as defined above such as meththio, ethylthio, n-propylthio, i-propylthio, n-butylthio, hexylthio, including their isomers. "Lower alkylthio" as used herein denotes an alkylthio group with a "lower alkyl" group as previously defined. "$C_{1-10}$ alkylthio" as used herein refers to an —S-alkyl wherein alkyl is $C_{1-10}$. "Phenylthio" is an "arylthio" moiety wherein aryl is phenyl.

The terms "alkylcarbonylamino" and "arylcarbonylamino" as used herein refers to a group of formula —NC(=O)R wherein R is alkyl or aryl respectively and alkyl and aryl are as defined herein.

The terms "alkylsulfinyl" and "arylsulfinyl" as used herein refers to a group of formula —S(=O)R wherein R is alkyl or aryl respectively and alkyl and aryl are as defined herein The terms "alkylsulfonyl" and "arylsulfonyl" as used herein refers to a group of formula —S(=O)$_2$R wherein R is alkyl or aryl respectively and alkyl and aryl are as defined herein. The term "heteroalkylsulfonyl" as used herein refers herein denotes a group of formula —S(=O)$_2$R wherein R is "heteroalkyl" as defined herein.

The terms "alkylsulfonylamino" and "arylsulfonylamino" as used herein refers to a group of formula —NR'S(=O)$_2$R wherein R is alkyl or aryl respectively, R' is hydrogen or $C_{1-3}$ alkyl, and alkyl and aryl are as defined herein.

The term "heteroalkoxy" as used herein means an —O-(heteroalkyl) group wherein heteroalkyl is defined herein. "$C_{1-10}$ heteroalkoxy" as used herein refers to an —O-(heteroalkyl) wherein alkyl is $C_{1-10}$. Representative examples include, but are not limited to, 2-dimethylaminoethoxy and 3-sulfonamido-1-propoxy.

The terms "halo," "halogen," and "halide" are used interchangeably herein and refer to fluoro, chloro, bromo, and iodo. "Haloalkyl" means alkyl as defined herein in which one or more hydrogen has been replaced with same or different halogen. Exemplary haloalkyls include —CH$_2$Cl, —CH$_2$CF$_3$, —CH$_2$CCl$_3$, —CF$_2$CF$_3$, —CF$_3$, and the like.

"Optionally substituted" means a substituent which is substituted independently with zero to three substituents selected from lower alkyl, halo, OH, cyano, amino, nitro, lower alkoxy, or halo-lower alkyl.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

Commonly used abbreviations include: acetyl (Ac), azo-bis-isobutyrylnitrile (AIBN), atmospheres (Atm), 9-borabicyclo[3.3.1]nonane (9-BBN or BBN), tert-butoxycarbonyl (Boc), di-tert-butyl pyrocarbonate or boc anhydride (BOC$_2$O), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propyl-ethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCl), ethyl (Et), ethyl acetate (EtOAc), ethanol (EtOH), 2-ethoxy-2H-quinoline-1-carboxylic acid ethyl ester (EEDQ), diethyl ether (Et$_2$O), O-(7-azabenzotriazole-1-yl)-N, N,N'N'-tetramethyl-uronium hexafluorophosphate acetic acid (HATU), acetic acid (HOAc), 1-N-hydroxybenzotriazole (HOBt), high pressure liquid chromatography (HPLC), iso-propanol (IPA), lithium hexamethyl disilazane (LiHMDS), methanol (MeOH), melting point (mp), MeSO$_2$— (mesyl or Ms), methyl (Me), acetonitrile (MeCN), m-chloroperbenzoic acid (MCPBA), mass spectrum (ms), methyl t-butyl ether (MTBE), N-bromosuccinimide (NBS), N-carboxyanhydride (NCA), N-chlorosuccinimide (NCS), N-methylmorpholine (NMM), N-methylpyrrolidone (NMP), pyridinium chlorochromate (PCC), pyridinium dichromate (PDC), phenyl (Ph), propyl (Pr), iso-propyl (i-Pr), pounds per square inch (psi), pyridine (pyr), room temperature (rt or RT), tert-butyldimethylsilyl or t-BuMe$_2$Si (TBDMS), triethylamine (TEA or Et$_3$N), 2,2,6,6-tetramethylpiperidine 1-oxyl (TEMPO), triflate or CF$_3$SO$_2$— (Tf), trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), thin layer chromatography (TLC), tetrahydrofuran (THF), trimethylsilyl or Me$_3$Si (TMS), p-toluenesulfonic acid monohydrate (TsOH or pTsOH), 4-Me-C$_6$H$_4$SO$_2$— or tosyl (Ts), N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

The metal ion(s) of the present disclosure are bound by the contrast agent. In some embodiments, the metal ion is Gadolinium (GdIII). In some embodiments, the metal ion is technetium. In some embodiments, the metal ion is indium. A person of skill in the art would understand that other metal ions suitable for use in contrast agents may also be used in the compounds of the present disclosure for example manganese, copper, copper 64 and iron.

The metal complexable portion of the contrast agent may be 1,4,7,10-tetraazacyclododecane tetraacetic acid (DOTA), diethylene triaminopentaacetic acid (DTPA), or variants thereof. Metal chelates are well known in the art and these compounds are often referred to as chelants, cheltors and chelating agents. The structure of the chelating agent is such that is forms a soluble, complex molecule with a metal ion and inactivates the metal ion from reacting with other elements or ions to produce precipitates. A person of skill in the art would understand that any chelating agent suitable for human administration would be suitable in the preparation of contrast agents according to present disclosure. In one embodiment, the metal complexable portion is DOTA. In another embodiment, the metal complexable portion is DTPA.

Specific examples of contrast agent compounds of the present disclosure include:

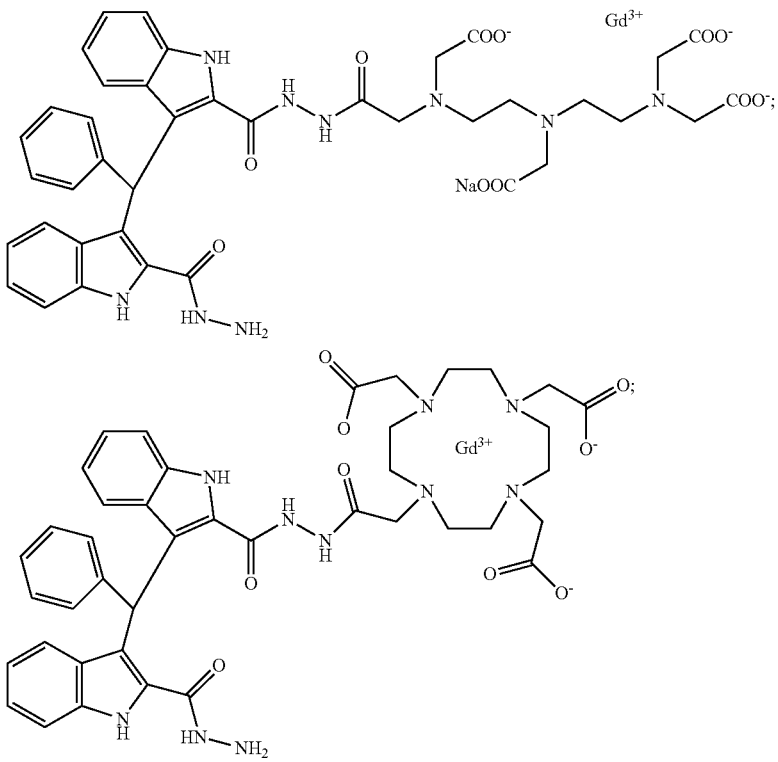

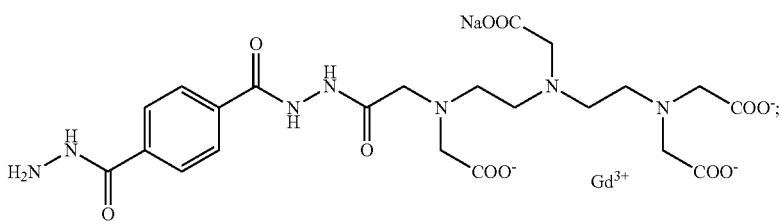

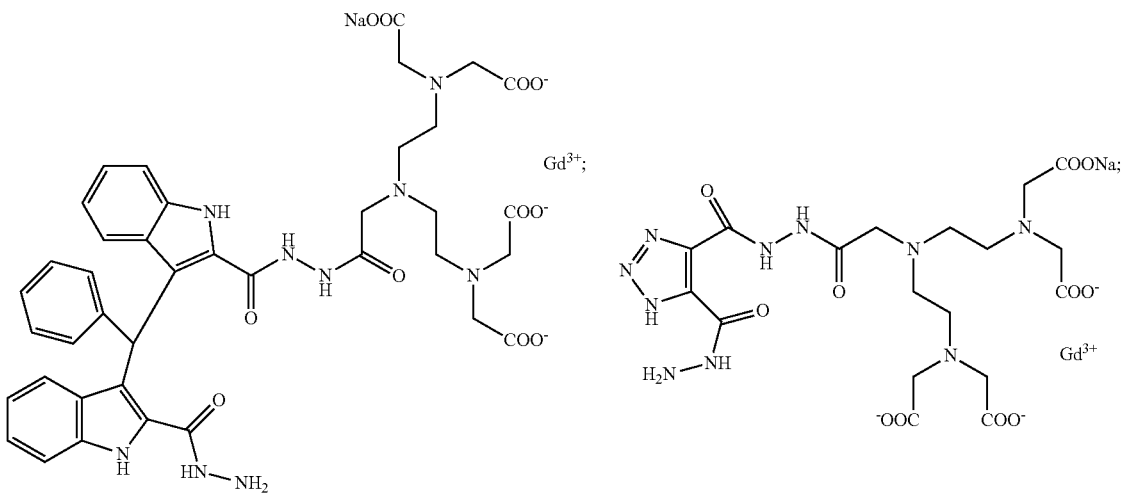

-continued

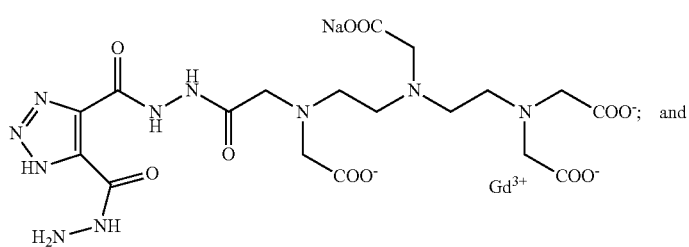
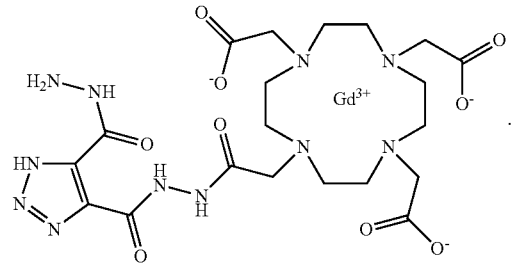

The contrast agent compounds of the present disclosure may be prepared by any conventional means.

The contrast agents may exhibit some quantitative differences with respect to their properties in medical applications, such as blood clearance (ranging from relatively fast to relatively slow), elimination from the body (predominantly by kidney or shifted to hepatobiliary secretion), and plasma protein binding (from low to high). Labeling/complexation of the contrast agents may be accomplished, using methods well known in the art, by chelation with radioactive or non-radioactive metal ions, preferably with ions of an element with an atomic number selected from 21 to 32, 37 to 39, 42 to 44, 49, 50 or 57 to 83 such as for example: —Mn, Fe or Gd (with respect to non-radioactive metals), and -99mTc, 111in, 64Cu, 67Ga, 90Y, 188Re, 186Re and 163Dy (with respect to radioactive metals).

Chelation with metal ions may be performed by methods well documented in the literature, at any stage of the production of the contrast agents, although most often in the final step. When protected functional groups are present in the metal-complexable portion of the compound, they may be partly or completely deprotected prior to metal chelation. Ionizable groups not involved in metal complexation may be optionally neutralized by acidic or basic counter-ions or by (inorganic and/or organic) compounds bearing ionizable acidic and/or basic groups. Remaining acidic protons, for example those that have not been substituted by the metal ion, can optionally be completely or partially replaced by cations of inorganic or organic bases, basic amino-acids or amino-acid amides. Suitable inorganic counter ions are for example, the ammonium ion, the potassium ion, the calcium ion, the magnesium ion and, more preferably, the sodium ion. Suitable cations of organic bases are, among others, those of primary, secondary or tertiary amines, such as, for example, ethanolamine, diethanolamine, morpholine, glucamin, N, N-dimethylglucamine, tris (hydroxymethyl) aminomethane and especially N-methylglucamine. Suitable cations of amino-acids are, for example, those of lysine, arginine and ornithine as well as the amides of any other acidic or neutral amino-acid such as for example lysine methylamide, glycine ethylamide or serine methylamide.

Contrast agents according to present disclosure localize to necrotic tissue, also referred to as dead tissue. On administration of the contrast agent, for example by intravenous injection, the contrast agent acts similar to a blood pool agent (also referred to as intravascular contrast agents). Following administration, a portion of the administered contrast agent localizes to necrotic tissue and a portion of the administered contrast agent remains in plasma. The portion of contrast agent in plasma is much greater that the portion localized to necrotic tissue. Thus, the contrast agents have a retention time, or half life, in plasma and a retention time, or half life, in necrotic tissue. The contrast agents according to the present disclosure demonstrate a similar retention time in plasma as compared to conventional contrast agents. For example, conventional contrast agents have a half life of about 30 to about 90 minutes, with virtually complete elimination of these agents within about 24 hours. Contrast agents of the present disclosure have a half life in plasma between about 30 minutes to 120 minutes, preferably 30 to 60 minutes. The contrast agent remaining in the plasma is eliminated via the urine. The portion of contrast agent localized to the necrotic tissue remains associated with the necrotic tissue for a period up to about 72 hrs. Traditional untargeted contrast agents are substantially cleared from a subject over a period of between 90 minutes and are almost completely eliminated after 24 hours. By comparison, the contrast agents of the present disclosure demonstrate a prolonged presence in necrotic tissue between about 48 to about 72 hours. The contrast agent localized to necrotic tissue highlights and improves visibility of necrotic tissue present.

In one embodiment, the presence of the contrast agent according to the present disclosure in necrotic tissue allows for the observation and identification of both the size and location of the necrotic tissue.

Tissue having suffered ischemic damage and cancerous tissue are not identifiable using traditional MRI technology as these tissues appear similar to healthy tissue. The contrast agents of the present disclosure allow for observation and/or identification of the size and/or location of infarcted tissue and/or cancerous tissue. In one aspect, the contrast agents facilitate the monitoring of death of cancerous tissue over time. In another aspect, the contrast agents facilitate improved patient care and enable a more precise medical diagnoses.

In some embodiments, contrast agents of the present disclosure may be used in vitro, in vivo and/or ex vivo, and may be administered directly or in the form of pharmaceutical compositions comprising the contrast agents in combination with at least one pharmaceutical acceptable carrier, as diagnostic agents and/or therapeutic agents. In one aspect, the contrast agents of the present disclosure are useful for the manufacture of compositions and/or medicaments suitable for use in diagnostic imaging or imaging-aided applications, including for example MRI, CT, SPECT, PET, MRI-aided applications, CT-aided applications, SPECT-aided applications or PET-aided applications. In another aspect, the contrast agents of the present disclosure are useful for the manufacture of diagnostic imaging agents or imaging-aided agents for use in the diagnostic imaging applications noted above. In a further aspect, the contrast agents may be used in vivo for visualizing and/or identifying organs, parts of organs, tissues, and parts of tissues for example necrotic tissue, and for visualizing and/or identifying diseases and pathologies. Contrast agents of the present disclosure may be useful in diagnosing diseases related to the presence of necrotic tissue. Such diseases that may be identified include ischemic insults for example myocardial or cerebral infarction, and space-occupying lesions for example tumors or inflammatory lesions that may be present in solid organs, for example the liver, kidney, spleen, and adrenal gland. Contrast agents of the present disclosure may be useful in differentiating between benign, pre-malignant or malignant tumors. These contrast agents may also be useful as a diagnostic tool in the evaluation of the effectiveness of a particular medical treatment, for instance in denoting the evolution or further evolution of necrosis.

In some embodiments, the contrast agents of the present disclosure may be useful in medical applications involving necrosis and necrosis-related pathologies, such as pathological or therapeutic necrosis caused by pathologic or therapeutically-induced ischemia or originating from trauma, radiation and/or chemicals, including therapeutic ablation, radiotherapy and/or chemotherapy, myocardial and cerebral infarctions. In this instance, the contrast agents are generally administered to a subject, intravenously, enterally or parenterally, as therapeutic and/or diagnostic agents. In one aspect, the contrast agent may be administered for use in the application of tumor ablation therapies, for example ischemic damage (i.e. pulmonary embolism, ischemic stroke, liver damage, kidney damage) to detect the extent of damage occurring in the affected tissue. The contrast agent localizes to the necrotic tissue of the tumor and indicates to a medical practitioner the tumor size and location and, in turn, allows for the continuous monitoring to track tumor size and indicate the effectiveness of a medical treatment method. The ability to monitor the effectiveness of an ongoing therapeutic treatment allows a subject to avoid undergoing ineffective medical treatment and, in turn, helps to develop patient-specific therapy. This is of particular value in fields where a wide variety of potential therapeutics are available, for example in cancer treatment a wide number of chemotherapeutics are available. Continually monitoring tumor size through the use of the contrast agents allows for an earlier assessment of the effectiveness of a particular chemotherapy and, in turn, allows a subject to avoid prolonged exposure to an ineffective line of treatment. The ability of the contrast agent to indicate the ineffectiveness of a medical treatment enables a medical practitioner to alter or change a course of medical treatment. Such a diagnostic tool allows for time saving measures and improvement of the overall patient outcome.

Pharmaceutically acceptable carriers for use in admixture with the contrast agents of the present disclosure are well known in the art and are selected based on the mode of administration of the contrast agent to the subject. In one aspect, a suitable formulation is a physiologically acceptable liquid formulation, preferably an aqueous solution or an emulsion or suspension including conventional surfactants such as polyethylene glycol.

In some embodiments, the contrast agents of the present disclosure provide a method for generating a diagnostic image of at least a part of a body of a subject following systemically or locally administering to the subject an effective amount of a contrast agent of the present invention. Preferably, the contrast agents of the present disclosure are used systemically as diagnostic agents by parenteral administration, including intravenous injection, at low doses. For example, when the metal ion of the contrast agent is gadolinium, a dosage range from about 10 to about 500 µmoles gadolinium per kg body weight, preferably from about 10 to about 200 µmoles gadolinium per kg body weight, more preferably from about 10 to about 100 µmoles gadolinium per kg body weight, and even more preferably from about 10 to about 50 µmoles gadolinium per kg body weight of the subject to be treated, wherein the gadolinium is bound to the metal-complexable portion of the contrast agent and the targeting portion is free to localize the contrast agent to necrotic tissue following administration of the contrast agent to a subject. In one aspect, the dose may comprise from about 5 µmoles/kg to about 1000 µmoles/kg (based on the mass of the subject), for example 5, 6, 7, 8, 9, 10, 15, 20, 25, 30, 35, 40, 45, 50, 55, 60, 65, 70, 75, 80, 85, 90, 95, 100, 120, 140, 160 180, 200, 250, 300, 350, 400, 450, 500, 750, 1000, µmoles/kg, or any amount therebetween; or from about 1 µmoles/kg to about 500 µmoles/kg or any amount therebetween, for example 1.0, 2.0, 5.0, 10.0, 15.0, 20.0, 25.0, 30.0, 35.0, 40.0, 45, 50.0, 55, 60.0, 65, 70.0, 75, 80.0, 85, 90.0, 95, 100, 120, 140, 160 180, 200, 250, 300, 350, 400, 450 500 µmoles/kg, or any amount therebetween; or from about 10 µmoles/kg to about 1000 ug/kg or any amount therebetween, for example 10.0, 11.0, 12.0 13.0, 14.0, 15.0, 20.0, 25.0, 30.0, 35.0, 40.0, 45, 50.0, 55, 60.0, 65, 70.0, 75, 80.0, 85, 90.0, 95, 100, 120, 140, 160 180, 200, 250, 300, 350, 400, 450, 500, 750, 1000 µmoles/kg, or any amount therebetween; or from about 20 µmoles/kg to about 1000 µmoles/kg or any amount therebetween, for example 20.0, 25.0, 30.0, 35.0, 40.0, 45, 50.0, 55, 60.0, 65, 70.0, 75, 80.0, 85, 90.0, 95, 100, 120, 140, 160 180, 200, 250, 300, 350, 400, 450, 500, 750, 1000 µmoles/kg.

Alternatively, the contrast agents of the present disclosure may also be useful for local administration, for example intracoronary administration in the case of a subject with myocardial infarction. Depending on the specific case, an effective local dose of the contrast agent of the present disclosure may be from about 0.1 to about 10 µmoles gadolinium per kg body weight, preferably from about 0.5 to about 7.5 µmoles gadolinium per kg body weight of the subject, more preferably from about 1 to about 5 µmoles gadolinium per kg body weight to be treated, wherein the gadolinium is bound to the metal-complexable portion of the contrast agent and the targeting portion is free to localize the contrast agent to necrotic tissue following administration of the contrast agent to a subject. In one aspect, the dose may comprise from about 0.1 µmoles/kg to about 10 µmoles/kg (based on the mass of the subject), for example 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 8.0, 8.5, 9.0, 9.5, 10.0 µmoles/kg, or any amount therebetween; or from about 0.5 µmoles/kg to about 7.5 µmoles/kg or any amount therebetween, for example 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5 µmoles/kg, or any amount therebetween; or from about 1 µmoles/kg to about 5 ug/kg or any amount therebetween, for example 0.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 µmoles/kg, or any amount therebetween.

One of skill in the art will be readily able to interconvert the units as necessary, given the mass of the subject, the concentration of the pharmaceutical composition, individual components or combinations thereof, or volume of the pharmaceutical composition, individual components or combinations thereof, into a format suitable for the desired application.

The pharmaceutical compositions of the invention may include an "effective amount", "therapeutically effective amount" or a "prophylactically effective amount" of a contrast agent of the invention. A "therapeutically effective amount" refers to an amount effective, at dosages and for periods of time necessary, to achieve the desired therapeutic result. A therapeutically effective amount of the contrast agent may be determined by a person skilled in the art and may vary according to factors such as the disease state, age, sex, and weight of the individual, and the ability of the contrast agent to elicit a desired response in the individual. A therapeutically effective amount is also one in which any toxic or detrimental effects of the contrast agent are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

In some embodiments, when a radioactive complexing metal such as indium-111 is used, the contrast agent may be administered with a radioactivity in the range of about 20 to 200 MBq (megabecquerels). When a radioactive complexing metal such as technetium-99 is used, the contrast agent may be administered with a radioactivity in the range of about 350 to 1,000 MBq.

Further aspects of the invention will become apparent from consideration of the ensuing description of the embodiments of the present disclosure. A person skilled in the art will realize that other embodiments of the invention are possible and that the details of the invention can be modified in a number of respects, all without departing from the inventive concept. Thus, the drawings, descriptions and examples are to be regarded as illustrative in nature and not restrictive.

EXAMPLES

The compounds of the present disclosure can be prepared by any conventional means. Suitable processes for synthesizing these compounds are provided in the Examples below.

Reagents were purchased from Sigma Aldrich or other suppliers as indicated below. However, reagents may also be purchased from other suppliers. Reactions were conducted using the equipment detailed below. The purification of the compounds was conducted by methods known to those skilled in the art, such as elution of silica gel column. However, other methods may also be used. Compound identities were confirmed by mass spectrometry.

Example 1

Preparation of RF1311: The preparation includes steps in Scheme 1.

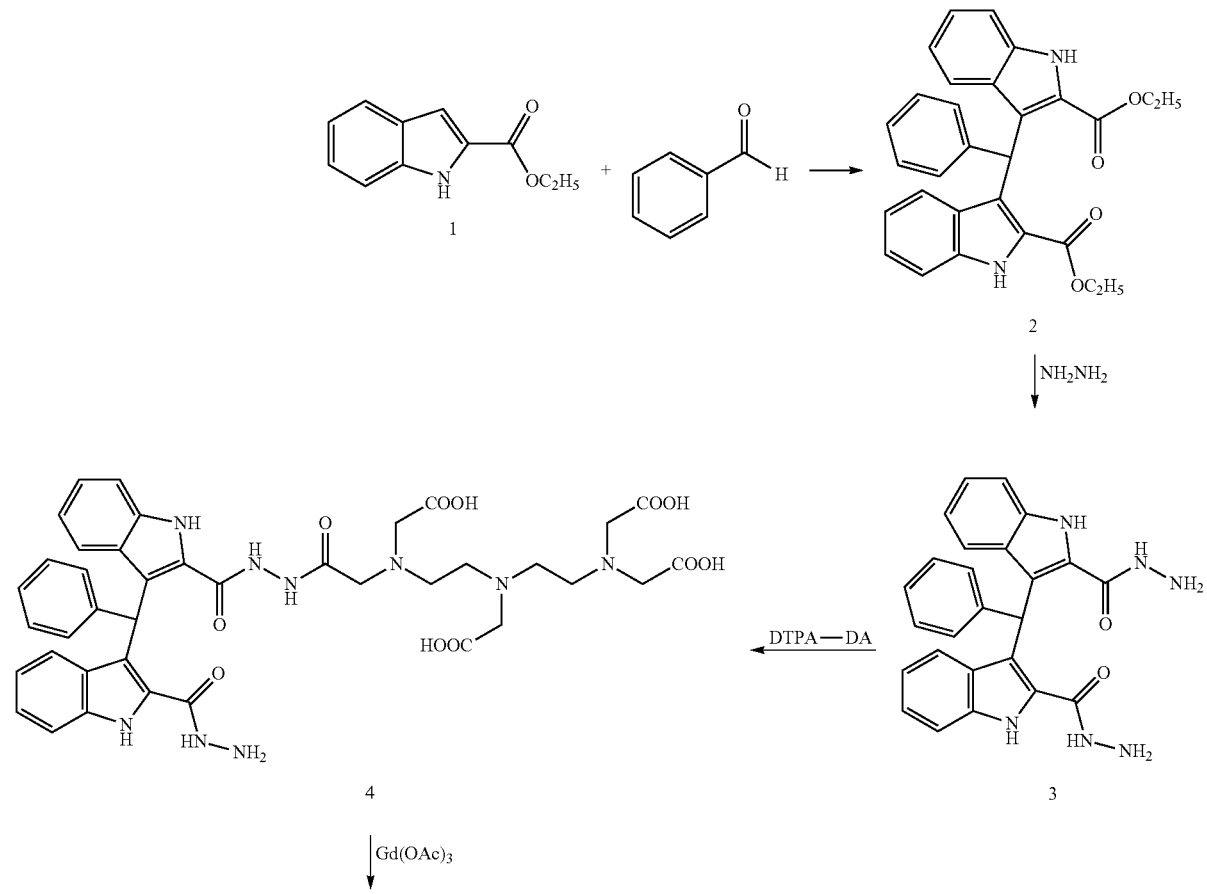

Scheme 1

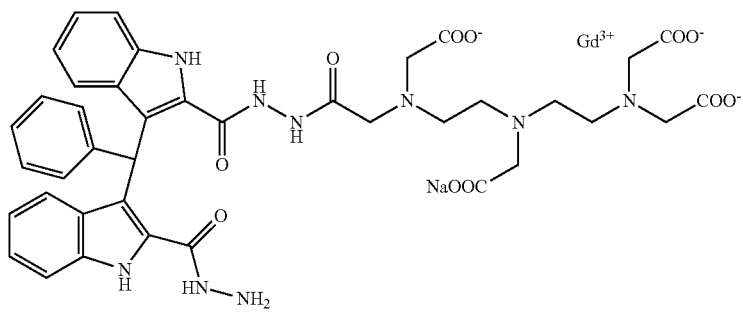

RF1311

Compound 2. Ethyl indole-2-carboxylate (18.9 g, 100 mmol) was dissolved in 200 ml ethanol under nitrogen atmosphere; benzaldehyde (5.3 g, 50 mmol) was added and the mixture was heated to reflux temperature. Concentrated HCl (3.7 ml) was added and the reaction was left for 2 hour. After cooling the white product was filtered off and washed thoroughly with cold ethanol. The reaction can be followed by TLC (CHCl$_3$:Hexane=1:1). Yield was 90%.

Compound 3. Compound 3 was prepared according the modified procedures of Cresens, Erwin et al. (PCT/BE01/00192). 5.0 g (10.7 mmol) of compound 2 and 10 g hydrazine monohydrate were dissolved in a mixture of 60 ml pyridine and 30 ml methanol. After refluxing the mixture for 48 hours, solvents were removed under reduced pressure. The residue was treated by adding H$_2$O, H$_2$O/methanol and then acetonitrile; after each addition, the solvent was removed under reduced pressure. Finally, the hydrazide was washed with acetonitrile and the precipitate was collected by filtration and dried over P$_2$O$_5$, yielding 3.4 g of the desired product 3. Identification thereof was confirmed by 1H-NMR spectroscopy. 1H-NMR (DMSO): 4.51 (br s, NHNH$_2$, 4H), 6.57-6.68 (m, ArH3, ArH4, 4H), 6.99-7.11 (m, ArH2, ArH, 4H), 7.21 (m, ArH, 3H), 7.27 (s, CH, 1H), 7.40 (d, ArH1, 2H), 9.62 (s, CONH, 2H), 11.40.

Compound 4. Compound 4 was prepared according the modified procedures of Platzek, Johannes and Niedballa, Ulrich (PCT Int. Appl., 2002059076). 3.57 g (10 mmol) of DTPA-bisanhydride was dissolved in 35 ml of dimethyl sulfoxide under an addition of 2.6 g (30 mmol) of lithium bromide (under gentle heating). The mixture was allowed to cool to 40° C., 0.18 g (10 mmol) of water was added, and the mixture was stirred for 10 minutes. This solution was added dropwise to a mixture of 4.38 g (10 mmol) of compound 3 and 2.02 g (20 mmol) of triethylamine within 30 minutes. The reaction mixture was stirred for 8 hours at 40° C. It was cooled to room temperature, To this solution, a mixture of 20 ml of acetone/180 ml of methyl tert-butyl ether (MTB) was added dropwise, and the mixture was stirred for one hour at room temperature. The deposited precipitate was filtered, washed 2 times with a little acetone, and dried (in vacuum/50° C.). For purification, it was chromatographed on silica gel (eluent: methanol/chloroform/formic acid=20:10:1). It was stirred with isopropanol/formic acid (20:1), the precipitate was extracted, and dried in vacuum/60° C. Yield: 1.65 g (20% of theory) of a colorless solid. Identification thereof was confirmed by 1H-NMR spectroscopy. 1H-NMR (D2O): 2.7-3.4 methylene hydrogens 18H; 6.6-7.5 aromatic hydrogens and —CH, 14H.

RF1311: Compound 4 (1.0 mmol) was dissolved in water (60 ml) and Gadolium (III) acetate (1.0 mmol) was added slowly. During the addition the pH was maintained at 7.4 with sodium hydroxide. After addition the mixture was stirred at room temperature over night. For desalting the mixture was applied on a C18-silicagel column that was rinsed with distilled water. Solvents were removed in vacuo and product was obtained as a white solid. Identity of the product was confirmed by mass spectrometry.

Example 2

Preparation of RF1401: The preparation includes steps in Scheme 2.

Scheme 2

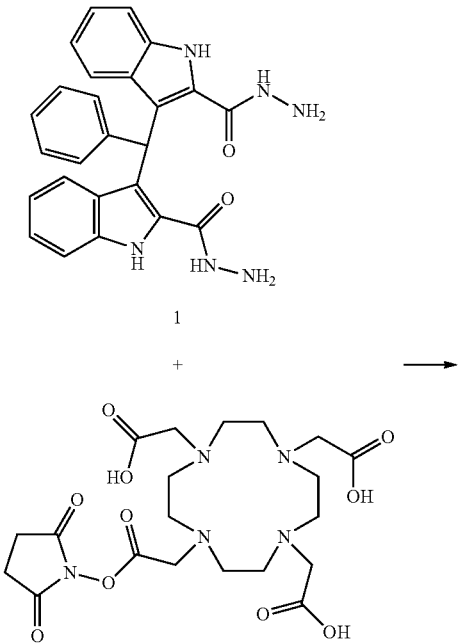

21
-continued

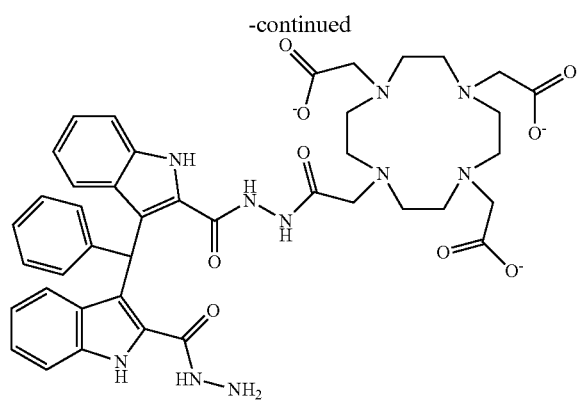

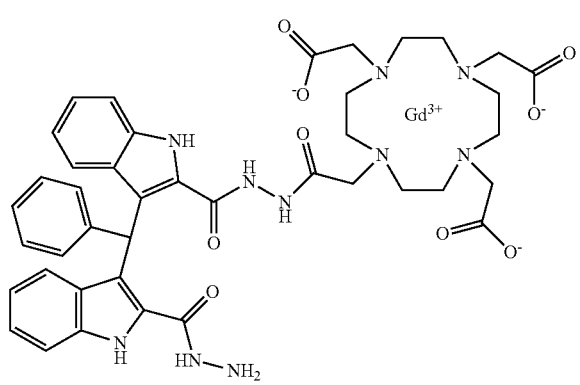

RF1401

Compound 2: compound 1 (0.876 g, 2 mmol), DOTA-NHS-ester (1.0 g, 2 mmol, (made according to the procedures of Li, C.; Wong and W.-T. *Tetrahedron,* 2004, 60, 5595-5560.) and DIPEA (0.284 g, 2.2 mmol) were dissolved in dry DMF (40 mL) and the resulting mixture was stirred for 24 h at room temperature. After addition of water the solvents were removed under reduced pressure and the resulting white powder was dissolved in a mixture of acetonitrile/H2O (1:1, v/v) and purified by preparative RP-HPLC. Yield: 0.59 g of white solid (0.72 mmol; 36%). 1H NMR (D2O) d 7.6-6.6, 14H, aromatic hydrogens and —CH; 3.7-3.0, 24H, methylene hydrogens.

RF1401: Compound 2 (0.5 mmol) was dissolved in water (30 ml) and Gadolium (III) acetate (0.5 mmol) was added slowly. During the addition the pH was maintained at 7.4 with sodium hydroxide. After addition the mixture was refluxed over night. For desalting the mixture was applied on a C18-silicagel column that was rinsed with distilled water. Solvents were removed in vacuo and product was obtained as a white solid. Identity of the product was confirmed by mass spectrometry.

22
Example 3

RF1402 was prepared as a control compound.
Preparation of RF1402: The preparation includes steps in Scheme 3

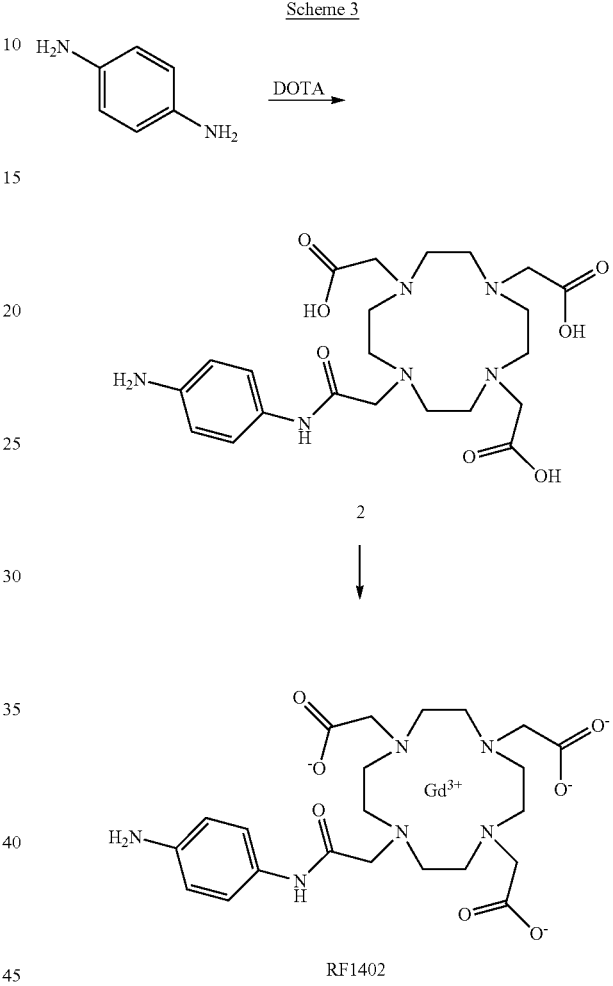

Compound 2: DOTA (2.2 g, 5 mmol) was dissolved in 100 ml of distilled water and NaOH was used to adjust pH to 4.8. The solution was cooled to 4° C. and stirred. N-Ethyl-N'-(3-dimethylaminopropyl) carbodiimide hydrochloride (EDCl, 1.92 g 10 mmol) was added followed by p-amino aniline (7 mmol). The mixture was stirred at 4° C. for 1 h and then room temperature for 24 h. Purification was conducted by the application of a preparative C 18 column (200 g). The column was eluted with 10% methanol in water. Pure fractions were combined and evaporated to dryness, yielding the desired product as a white solid.

RF1402: Compound 2 (1.0 mmol) was dissolved in water (60 ml) and Gadolium (III) acetate (1.0 mmol) was added slowly. During the addition the pH was maintained at 7.4 with sodium hydroxide. After addition the mixture was refluxed overnight. For desalting the mixture was applied on a C18-silicagel column that was rinsed with distilled water. Solvents were removed in vacuo and product was obtained as a white solid. Identity of the product was confirmed by mass spectrometry.

Example 4

RF1403 was prepared as a control compound.
Preparation of RF1403: The preparation includes steps in Scheme 4

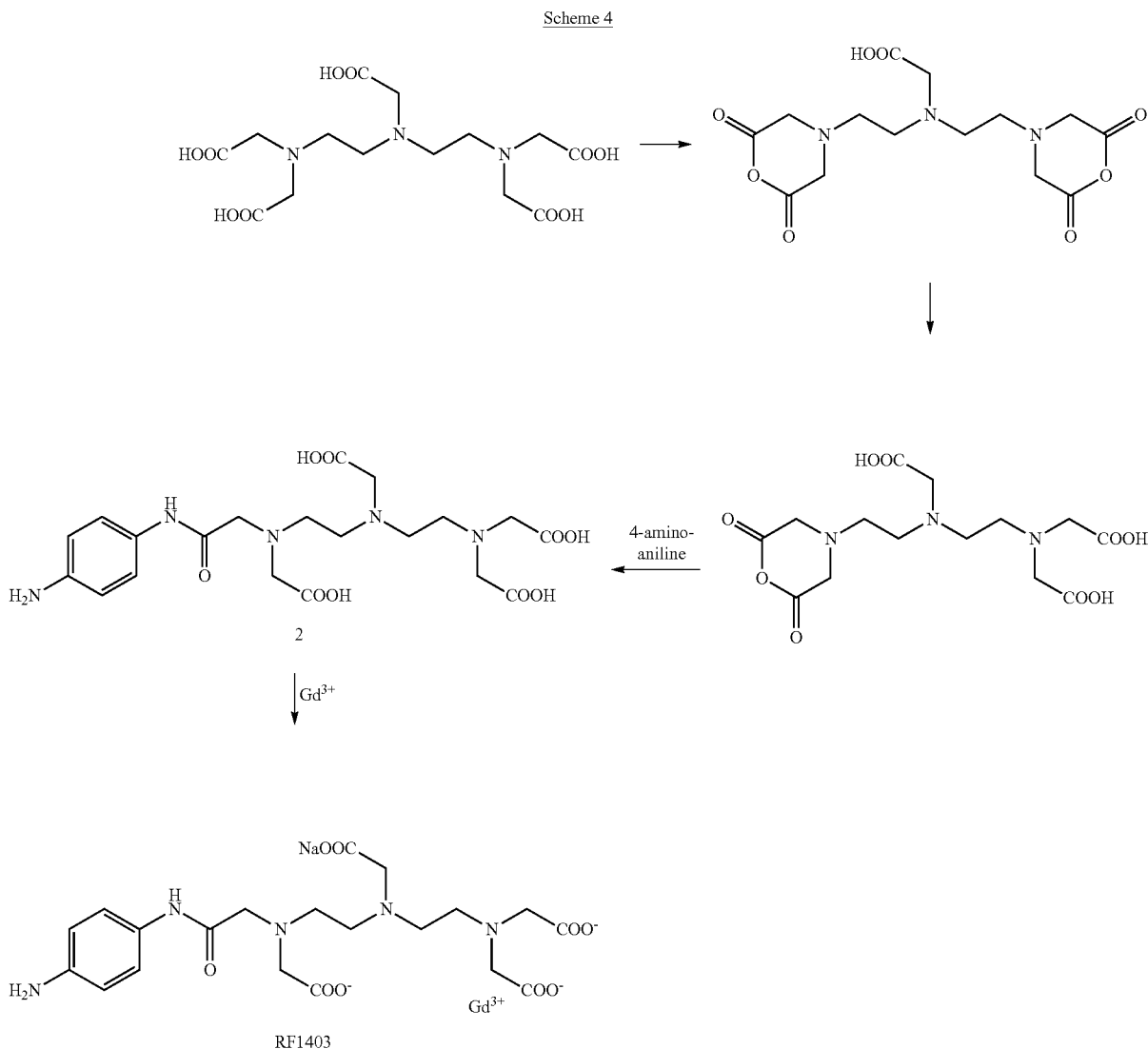

DTPA-Di-anhydrade: Diethylenetriaminepentaacetic acid (39.3 g, 0.1 mole) was suspended in pyridine (50 g), and acetic anhydride (40.8 g. 0.4 mole) was added. The mixture was heated at 65° C. for 24 hours. The product was filtered, washed with acetic anhydride and ether, and dried.

Compound 2: To a solution of DTPA-bisanhydride (3.57 g, 10 mmole) and triethylamine (5 ml) in 40 ml of dimethylformamide (DMF) was slowly added 0.18 g of water (10 mmole) in 10 ml of dry DMF over a period of 2 hours. p-amino aniline (10 mmol) was added and the reaction mixture was stirred overnight. After evaporation to dryness, the residue was evaporated to dryness. The resulting white powder was dissolved in a mixture of acetonitrile/H2O (1:1, v/v) and purified by preparative RP-HPLC. Yield: 0.59 g of white solid (0.72 mmol; 36%).

RF1403: the compound 2 (1.0 mmol) was dissolved in water (60 ml) and Gadolium (III) acetate (1.0 mmol) was added slowly. During the addition the pH was maintained at 7.4 with sodium hydroxide. After addition the mixture was refluxed overnight. For desalting the mixture was applied on a C18-silicagel column that was rinsed with distilled water. Solvents were removed in vacuo and product was obtained as a white solid. Identity of the product was confirmed by mass spectrometry.

Example 5

Preparation of RF1404: The preparation includes steps in Scheme 5.

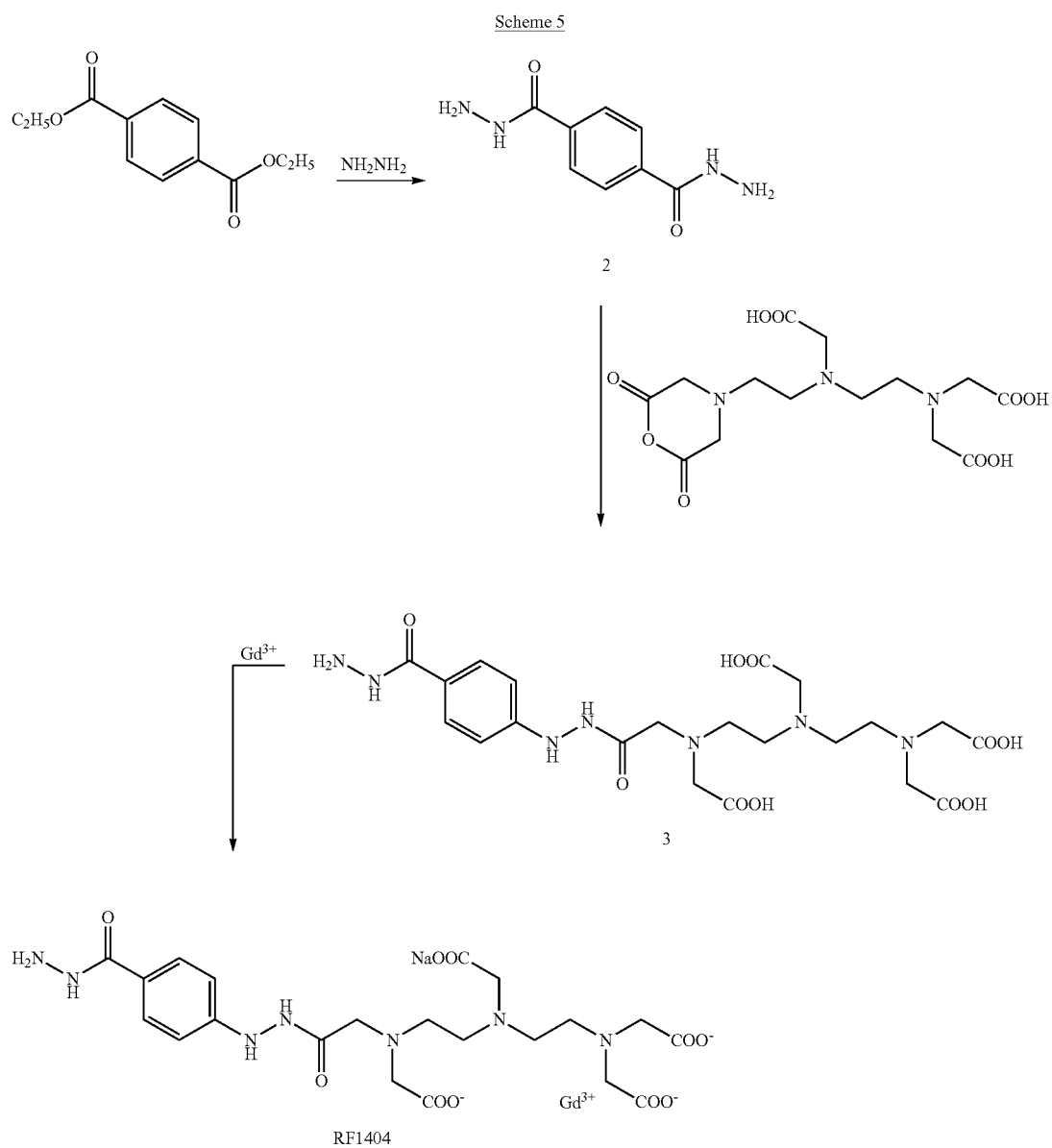

Scheme 5

Compound 2: 4.44 g (20 mmol) of diethyl terephthalate and 10 g hydrazine monohydrate were dissolved in a mixture of 80 ml pyridine and 40 ml methanol. After refluxing the mixture for 48 hours, solvents were removed under reduced pressure. The residue was treated by adding $H_2O$, $H_2O$/methanol and then acetonitrile; after each addition, the solvent was removed under reduced pressure. Finally, the hydrazide was washed with acetonitrile; the precipitate was collected by filtration and dried over $P_2O_5$, yielding 2.62 g of the desired product 2. (10.16 mmol, 50%).

Compound 3: To a solution of DTPA-bisanhydride (3.57 g, 10 mmole) and triethylamine (5 ml) in 40 ml of dimethylformamide (DMF) was slowly added 0.18 g of water (10 mmole) in 10 ml of dry DMF over a period of 2 hours. Compound 2 (10 mmol) was added and the reaction mixture was stirred overnight. After evaporation to dryness, the residue was evaporated to dryness. The resulting white powder was dissolved in a mixture of acetonitrile/H2O (1:1, v/v) and purified by preparative RP-HPLC. Yield: 0.68 g of white solid (1.1 mmol; 11%).

RF1404: the compound 3 (1.0 mmol) was dissolved in water (60 ml) and Gadolium (III) acetate (1.0 mmol) was added slowly. During the addition the pH was maintained at 7.4 with sodium hydroxide. After addition the mixture was stirred at room temperature overnight. For desalting the mixture was applied on a C18-silicagel column that was rinsed with distilled water. Solvents were removed in vacuo and product was obtained as a white solid. Identity of the product was confirmed by mass spectrometry.

Example 6
Preparation of RF1211: The preparation includes steps in Scheme 6.
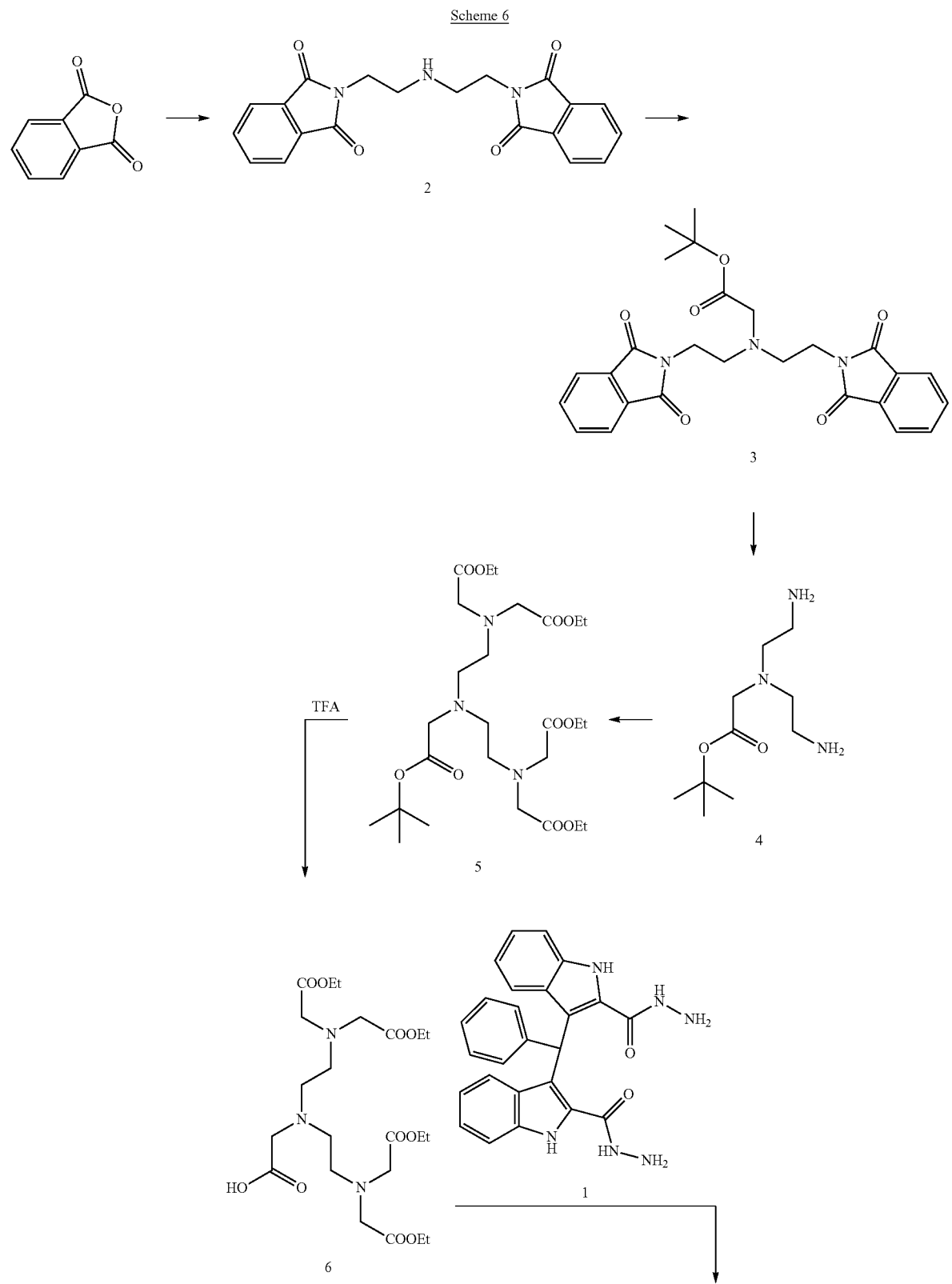
Scheme 6

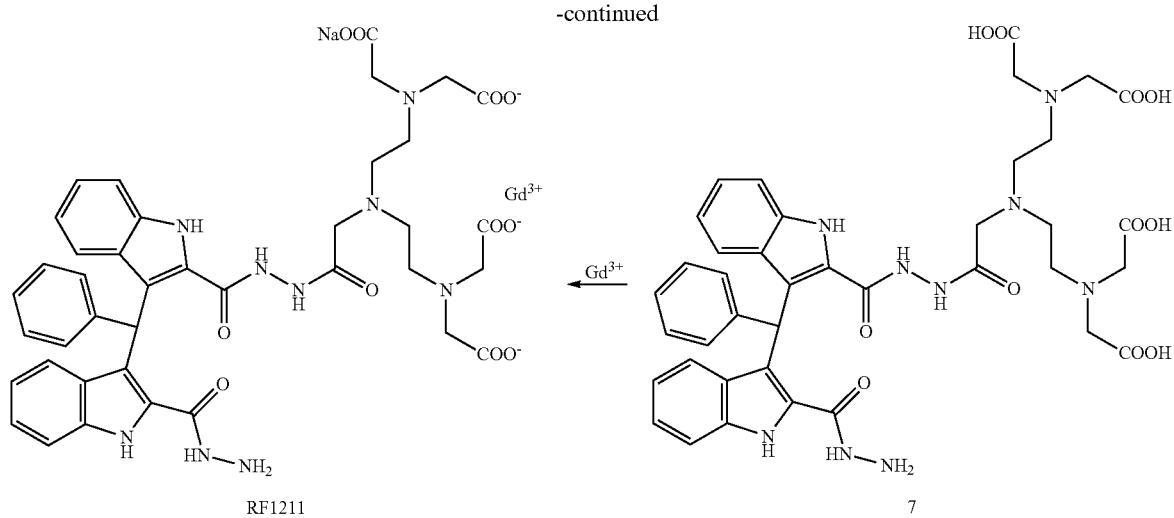

RF1211

1,5-Diphthalimido-3-azapentane (2) Compound 2 was prepared by a previously published procedure (J. AM. CHEM. SOC. 2004, 126, 823-833): a mixture of 1,5-diamino-3-azapentane (10.3 g, 0.10 mol) and phthalic anhydride (33.2 g, 0.20 mol) in 160 mL of glacial acetic acid was refluxed for 4 h. The solvent was removed under reduced pressure, and then 160 mL of hot ethanol was added with stirring until a solid appeared. The product was collected and washed with cold ethanol. Yield 23.9 g (81%), mp 181-183□C, 1H NMR (DMSO-d6, 300 MHz): 7.79 (m, 4H, H3', 6'), 7.74 (m, 4H, H4', 5'), 3.59 (t, J) 6.3 Hz, 4H, H1, 5), 2.76 (t, 4H, H2, 4). 13C NMR (75 MHz, DMSO-d6): 167.85 (CO), 134.10 (C4', 5'), 131.63 (C1', 2'), 122.74 (C3', 6'), 46.16 (C2, 4), 37.18 (C1, 5). MS (ES+, MeOH): m/z 364 (MH+).

t-Butyl 1,7-dinaphthoyl-4-diethylenetriamine acetate (3) Compound 3 was prepared by a previously published procedure (J. Peptide Sci. 8: 663-670, 2002): a mixture of triamine derivative (2) (13.3 mmol, 4.8 g), t-butyl 2-bromoacetate (21.8 mmol, 3.5 ml) and DIPEA (13.3 mmol, 2.3 ml) in dichloromethane (100 ml) was refluxed for 36 h, under nitrogen. It was then washed with 10% citric acid (50 ml), sodium hydrogen carbonate (1 M, 50 ml) and distilled water (50 ml). The organic layer was dried over MgSO4, filtered and evaporated to dryness. The resulting oily product was recrystallized from ethanol, filtered and washed with ice-cold ethanol to give t-butyl 1,7-dinaphthoyl-4-diethylenetriamine acetate (3) as a white solid (51% yield), m.p. 119° C.-121° C. 1H-NMR: CDCl3 1.42 (9H, s, C(CH3)3), 3.01-3.04 (4H, t, J 6.5, 2×CH2), 3.45 (2H, s, CH2), 3.70-3.74 (4H, t, J 6.5, 2×CH2NPht), 7.64-7.72 (8H, m, 2×Pht); 13C-NMR: CDCl3 21.2 (But CH3), 36.0, 51.6 (CH2), 81.0 (But C), 123.0 (aromatic CH), 132.1 (aromatic C), 133.7 (aromatic CH), 168.2, 170.5 (CO); FAB-m/z [M+H]+=478, [M+Na]+=500; $C_{26}H_{27}N_3O_6$ requires 478.1978 t-Butyl-4-diethylenetriamine acetate (4) To a solution of t-butyl 1,7-dinaphthoyl-4-diethylenetriamine acetate (3) (4.19 mmol) in 95% acetonitrile/water (40 ml), 4 mmol equivalent of hydrazine hydrate was added and the reaction mixture stirred at room temperature, until HPLC analysis showed no starting material to be present (40 h). The resulting white precipitate was filtered, washed with acetonitrile, and the combined filtrates were evaporated using a rotary evaporator at 25° C. under high vacuum to give t-butyl-4-diethylenetriamine acetate (4) as a colourless solid (87% yield); 1H-NMR, d6 DMSO, 1.10 (9H, s, C (CH3)3), 2.59-2.71 (4H, m, 2×CH2), 2.91 (2H, s, NCH2CO2), 3.26-3.47 (4H, m, 2×CH2NH2), 4.20-4.70 (4H, br s, 2×NH2); 13C-NMR d6 DMSO 27.8 (But CH3), 37.3, 48.7 (CH2), 80.4 (But C), 167.8 (CO); Cl-m/z [M+H]+=218.

[Bis[2-bis(ethoxycarbonylmethylamino)ethyl]amino]acetic Acid tert-Butyl Ester (5) Compound 5 was prepared by a previously published procedure (Synthesis 2004, No. 11, 1835-1843): to an ice-cooled solution of compound 4 (1.1 g, 5.0 mmol) and ethyl bromoacetate (3.9 g, 25 mmol) in anhyd MeCN (30 mL) was added i-Pr2NEt (1.29 g, 10.0 mmol), maintaining the reaction temperature below 0° C. After the mixture was stirred overnight at r.t., the solution was concentrated at reduced pressure. The residue was taken up in EtOAc (50 mL) and washed with aq sat. NaHCO3 (2×25 mL) and brine (25 mL). The organic phase was dried (Na2SO4), filtered and evaporated. The product, after silica gel flash chromatography (CH2Cl2-MeOH, 98:2), was recovered as a colorless oil (1.50 g, 51%). IR (CHCl3): 1734, 1372, 1205 cm-1. 1H NMR (CDCl3): d=1.24 (t, 12 H, J=7.5 Hz, 4×OCH2CH3), 1.42 [s, 9 H, (CH3)3C], 2.85 (s, 8 H, 2×NCH2CH2N), 3.30 (s, 2 H, CH2CO2Bu-t), 3.50 (s, 8 H, 4×CH2CO2Et), 4.16 (q, 8 H, J=7.5 Hz, OCH2CH3). Anal. Calcd for C26H47N3O10: C, 55.60; H, 8.43; N, 7.48. Found: C, 55.82; H, 8.59; N, 7.76.

[Bis[2-bis(ethoxycarbonylmethylamino)ethyl]amino]acetic Acid (6) A solution of 5 (1.46 g, 2.60 mmol) in TFA (2.0 mL) was allowed for 2 h at r.t. After evaporation of TFA at reduced pressure, the residue was repeatedly co-evaporated with anhydrous $Et_2O$ and then purified on silica gel (CHCl3-i-PrOH, 80:20). The product was recovered as a colorless oil (600 mg, 46%). IR ($CHCl_3$): 2958, 1737, 1380, 1211 $cm^{-1}$. 1H NMR (CDCl3): d=1.21 (t, 12 H, J=7.5 Hz, 4×$OCH_2CH_3$), 3.10 (s, 8 H, 2×$NCH_2CH_2N$), 3.55 (s, 8 H, 4×$CH_2CO_2Et$), 3.62 (s, 2 H, $CH_2CO_2$ H), 4.12 (q, 8 H, J=7.5 Hz, $OCH_2CH_3$), 11.20 (s, 1 H, $CO_2H$).

Compound 7: A dispersion of the bis-hydrazide 1 (3.3 g, 7.5 mmol) in a mixture of DMF (50 mL) and triethylamine (5 mmol) was sonicated for 15 min. TBTU (1.9 g, 6 mmol) was added and the mixture was sonicated again for 15 min. Product 6 (3.5 g, 6.9 mmol) was added and the mixture was stirred for 3 h. After removal of the solvent, the residue was dissolved in a concentrated solution of $NaHCO_3$. The pH was adjusted to 12 with 5N NaOH and stirred for 2 h. The resulting mixture was evaporated and placed on a C18 reversed-phase column, which was then eluted successively with 0.2 L of a solution of ammonium acetate in distilled water (0.1 m) containing 3% methanol, 0.2 L of a solution containing 5% methanol, and finally with 0.5 L of a solution containing 10% methanol. The product was collected in 50 mL fractions and the purity was checked by conducting HPLC and monitoring the peak eluting at 11 min. Yield: 0.82 g of yellow solid; 1H NMR (500 MHz, D2O): d=3.04 (m, 4H), 3.30 (m, 6H), 3.55 (s, 4H), 3.70 (s, 4H), 6.68 (s, 2H), 6.82 (m, 2H), 7.21 (m, 4H), 7.32 (m, 4H), 7.56 ppm (m, 2H)

RF1211: Compound 7 (0.5 mmol) was dissolved in water (30 ml) and Gadolium (III) acetate (0.5 mmol) was added slowly. During the addition the pH was maintained at 7.4 with sodium hydroxide. After addition the mixture was refluxed overnight. For desalting the mixture was applied on a C18-silicagel column that was rinsed with distilled water. Solvents were removed in vacuo and product was obtained as a white solid. Identity of the product was confirmed by mass spectrometry.

Example 7

Preparation of RF1221: The preparation includes steps in Scheme 7.

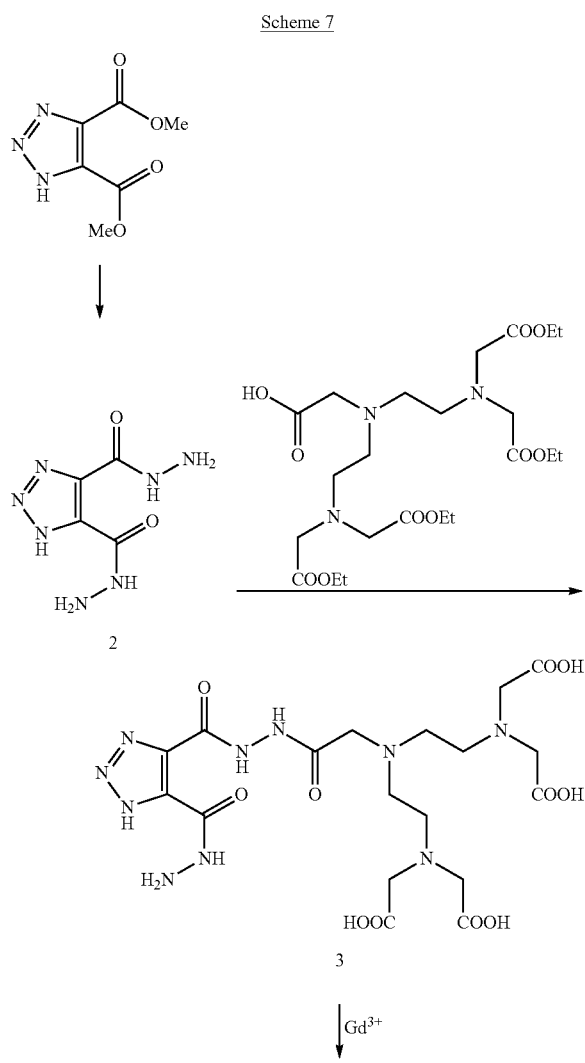

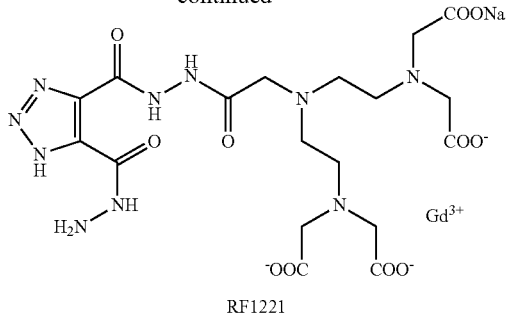

1H-1,2,3-triazole-4,5-dihydrazide (2). Methyl 1H-1,2,3-triazole-4,5-dicarboxate (3.7 g, 20 mmol) and 15 g hydrazine monohydrate were dissolved in a mixture of 60 ml pyridine and 30 ml methanol. After refluxing the mixture for 48 hours, solvents were removed under reduced pressure. The residue was treated by adding $H_2O$, $H_2O$/methanol and then acetonitrile; after each addition, the solvent was removed under reduced pressure. Finally, the hydrazide was washed with acetonitrile and the precipitate was collected by filtration and dried over $P_2O_5$, yielding 2.4 g of the desired product 2. Identification thereof was confirmed by 1H-NMR spectroscopy.

Compound 3 Compound 2 (1.4 g, 7.5 mmol) in a mixture of DMF (50 mL) and triethylamine (5 mmol) was sonicated for 15 min TBTU (1.9 g, 6 mmol) was added and the mixture was sonicated again for 15 min. DTPA-tetraester (3.5 g, 6.9 mmol, from Example-6) was added and the mixture was stirred for 3 h. After removal of the solvent, the residue was dissolved in a concentrated solution of $NaHCO_3$. The pH was adjusted to 12 with 5N NaOH and stirred for 2 h. The resulting mixture was evaporated and placed on a C18 reversed-phase column, which was then eluted successively with 0.2 L of a solution of ammonium acetate in distilled water (0.1 m) containing 3% methanol, 0.2 L of a solution containing 5% methanol, and finally with 0.5 L of a solution containing 10% methanol. The product was collected in 50 mL fractions and the purity was checked by conducting HPLC. Yield: 1.05 g of yellow solid (25%). Identification thereof was confirmed by 1H-NMR spectroscopy.

RF1221: Compound 3 (0.5 mmol) was dissolved in water (30 ml) and Gadolium (III) acetate (0.5 mmol) was added slowly. During the addition the pH was maintained at 7.4 with sodium hydroxide. After addition the mixture was refluxed overnight. For desalting the mixture was applied on a C18-silicagel column that was rinsed with distilled water. Solvents were removed in vacuo and product was obtained as a white solid. Identity of the product was confirmed by mass spectrometry.

Example 8

Preparation of RF1231: The preparation includes steps in Scheme 8.

Scheme 8

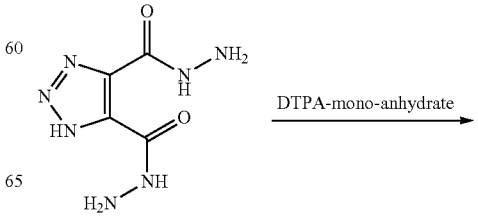

-continued

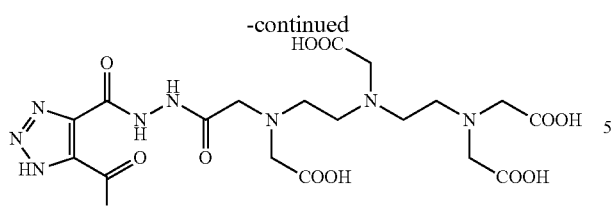

2

| Gd³⁺

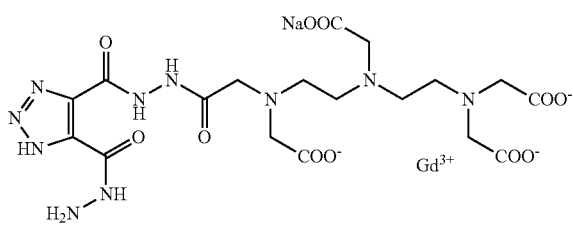

RF1231

Compound 2: Compound 2 was prepared according the modified procedures of Platzek, Johannes and Niedballa, Ulrich (PCT Int. Appl., 2002059076). 3.57 g (10 mmol) of DTPA-bisanhydride was dissolved in 35 ml of dimethyl sulfoxide under an addition of 2.6 g (30 mmol) of lithium bromide (under gentle heating). It was cooled to 40° C., and 0.18 g (10 mmol) of water was added, and the mixture was stirred for 10 minutes. This solution was added dropwise to a mixture of 1H-1,2,3-triazole-4,5-dihydrazide (1.85 g, 10 mmol) and 2.02 g (20 mmol) of triethylamine. The reaction mixture was stirred for 8 hours at 40° C. To this solution, a mixture of 20 ml of acetone/180 ml of methyl tert-butyl ether (MTB) was added dropwise, and the mixture was stirred for one hour at room temperature. The deposited precipitate was filtered, washed 2 times with a little acetone, and dried (in vacuum/50° C.). For purification, it was chromatographed on silica gel (eluent: methanol/chloroform/formic acid=20:10:1). It was stirred with isopropanol/formic acid (20:1), the precipitate was extracted, and dried in vacuum/60° C. Yield: 1.01 g (18% of theory) of a colorless solid. Identification thereof was confirmed by 1H-NMR spectroscopy.

RF1231: Compound 2 (0.5 mmol) was dissolved in water (30 ml) and Gadolium (III) acetate (0.5 mmol) was added slowly. During the addition the pH was maintained at 7.4 with sodium hydroxide. After addition the mixture was refluxed overnight. For desalting the mixture was applied on a C18-silicagel column that was rinsed with distilled water. Solvents were removed in vacuo and product was obtained as a white solid. Identity of the product was confirmed by mass spectrometry.

Example 9

Preparation of RF1241: The preparation includes steps in Scheme 9.

Scheme 9

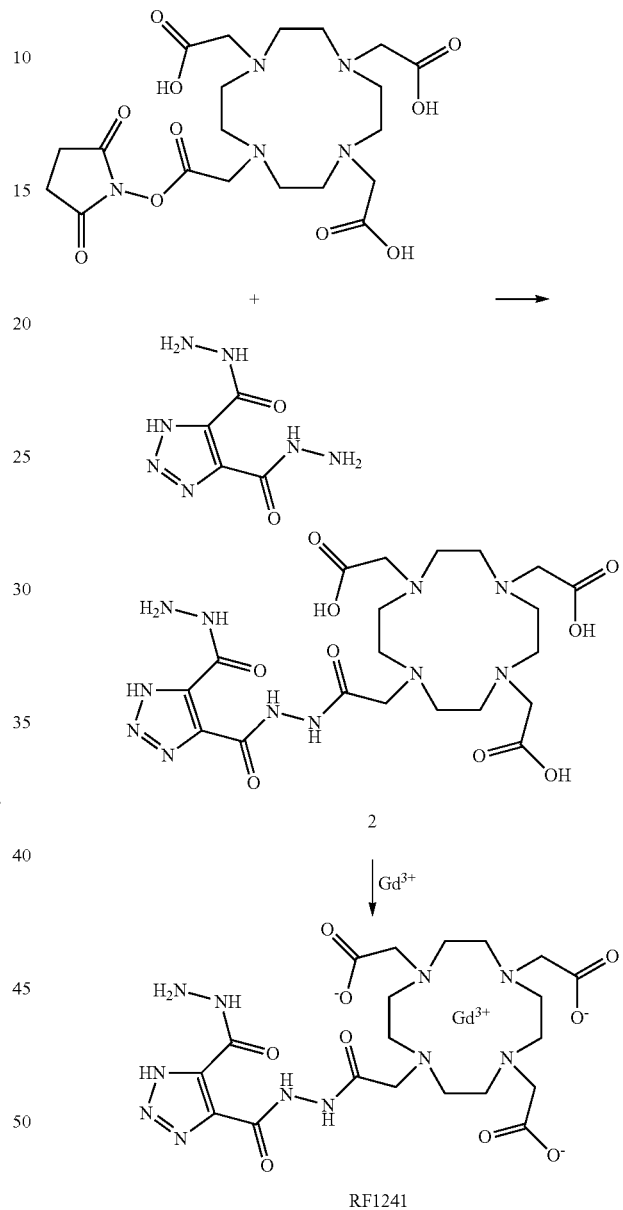

RF1241

Compound 2: 1H-1,2,3-triazole-4,5-dihydrazide (1.11 g, 6 mmol), DOTA-NHS-ester (3.0 g, 6 mmol, made according to the procedures of Li, C.; Wong and W.-T. *Tetrahedron*, 2004, 60, 5595-5560.) and DIPEA (0.852 g, 6.6 mmol) were dissolved in dry DMF (100 mL) and the resulting mixture was stirred for 24 h at room temperature. After addition of water the solvents were removed under reduced pressure and the resulting white powder was dissolved in a mixture of acetonitrile/H2O (1:1, v/v) and purified by preparative RP-HPLC. Yield: 1.13 g of white solid (33%).

RF1241: Compound 2 (0.5 mmol) was dissolved in water (30 ml) and Gadolium (III) acetate (0.5 mmol) was added slowly. During the addition the pH was maintained at 7.4 with sodium hydroxide. After addition the mixture was refluxed overnight. For desalting the mixture was applied on a C18-silicagel column that was rinsed with distilled water. Solvents were removed in vacuo and product was obtained as a white solid. Identity of the product was confirmed by mass spectrometry.

Example 10

MRI Analysis of Contrast Agents In Vivo

Methods and Materials

Contrast agents were prepared following the methods outlined in Example 1 above. Rats (250-300 g) were used for the following studies detailed below.

All treatment and testing was conducted during the light hours. Animals were housed and tested in compliance with the guidelines described in the European Guidelines for Animal Welfare. All experiments were conducted in and approved by the University of Leuven.

MRI in Rats

Rats were anesthetized by administration of isoflurane (5% induction, 1-2% maintenance) and positioned in an animal holder. The blood pressure and heart rate of the rats were monitored prior to ligation to provide a baseline condition. The rats were subjected to ligation of the hepatic artery under aseptic conditions for a period of 2 h. The ligature was then removed to allow for the reperfusion of the infarcted hepatic tissue. Following the ligation procedure, bupivacaine and Cicatrin were applied to the incision. The incision was closed in layers, and ketoprofen (5 mg/kg) was injected subcutaneously to treat inflammation.

In addition, muscle necrosis was induced by bolus injection of ethanol into the lateral dorsal muscle. This was monitored at the same time as the hepatic necrosis.

The contrast agent was intravenously injected 4 hours following the start of reperfusion. The blood pressure and heart rate were monitored during the ligation procedure and the administration of the contrast agent. The body temperature of the rats was monitored with a rectal probe and maintained at the physiological level by the circulating warm water. The rats were individually housed following their recovery from the anesthesia.

Between about 4 to 36 hours following the administration of the contrast agent, the rats were anesthetized by an intramuscular injection of thiobutabarbital (100 mg/kg) and transported to the MRI facility in the University of Leuven.

Total imaging time was approximately 60 minutes.

The rats were then immediately euthanized by administration of an overdose of pentobarbital (>120 mg/kg).

Results

Results RF1311

Figure 2:
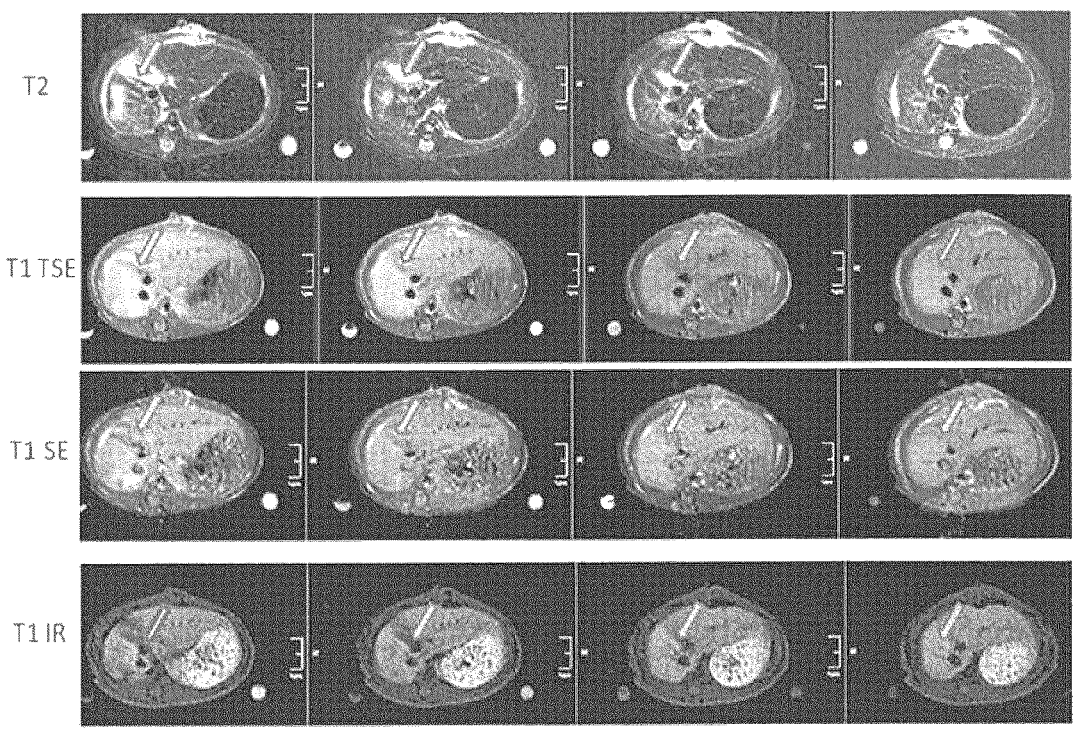
FIG. 2 shows magnetic resonance images of rat liver 24 hours after administration of contrast agent RF1311 at a dose of 40 mg/kg.
Figure 3:
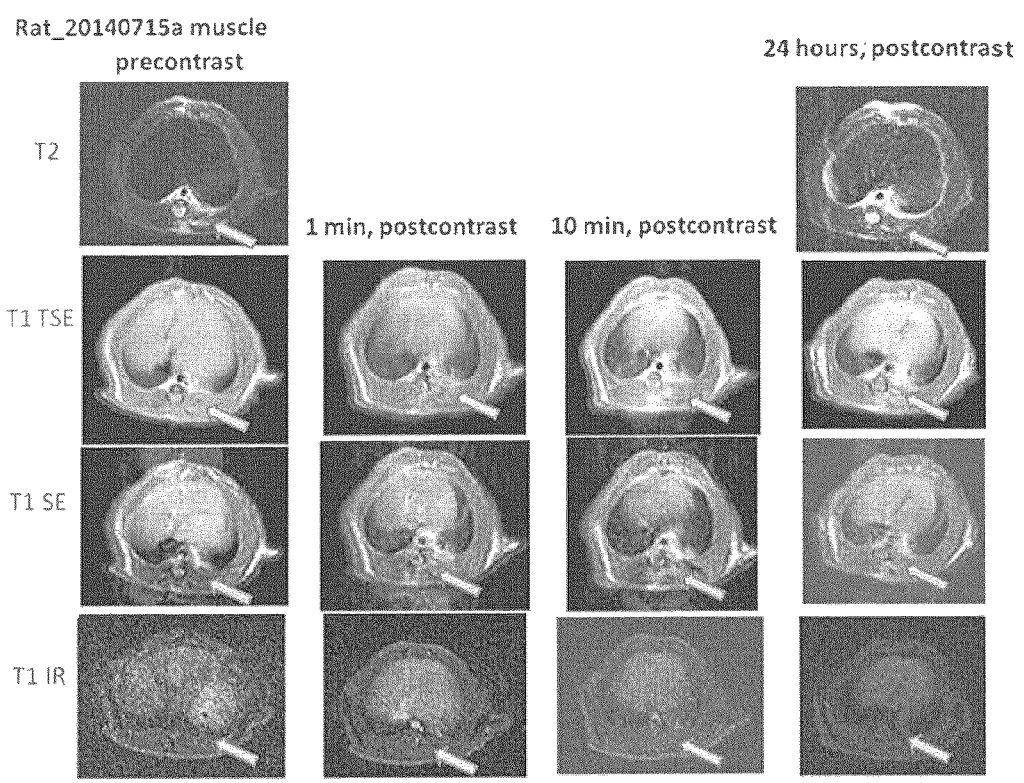
FIG. 3 shows magnetic resonance images of rats exhibiting alcohol-induced muscle necrosis. In column 1, the MRI images are prior to RF1311 administration. In column 2, the MRI images are 1 minute after RF1311 administration. In column 3, the MRI images are 10 minutes after RF1311 administration. In column 4, the MRI images are 24 hours after RF1311 administration.
Figure 4:
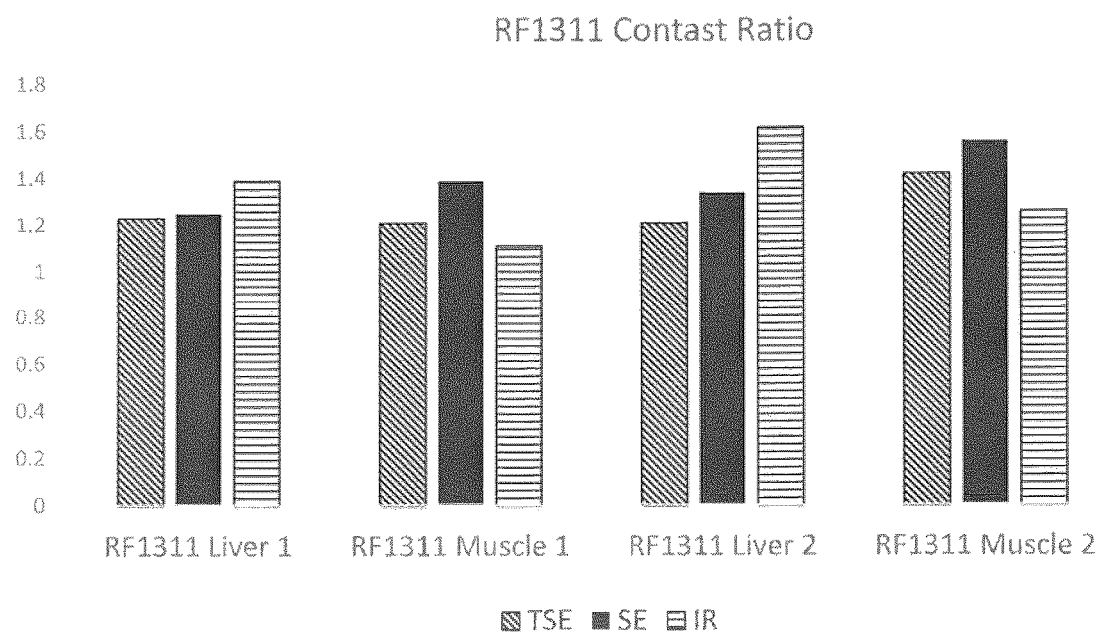
FIG. 4 is a graph illustrating the contrast ratios in Rat Infarcted Tissue for RF1311 in Liver and Muscle.

Contrast agent RF1311 was prepared following the method outlined in Example 1 above. Following the above-noted procedure, two groups of rats were administered contrast agent RF1311 at a dose of 40 mg/kg. The resultant MR image and corresponding tissue sample are shown in FIGS. 1, 2 and 3. The summary of contrast ratios with respect to time is shown in FIG. 4. This demonstrates the clear effect of RF1311 in differentiating necrotic from healthy tissue.

The results illustrate the necrotic tissue visible in the MR images. These results indicate that the contrast agent localized to the necrotic tissue portion of the tissue sample.

Example 11

Pharmacokinetics and Toxicology

Figure 5:
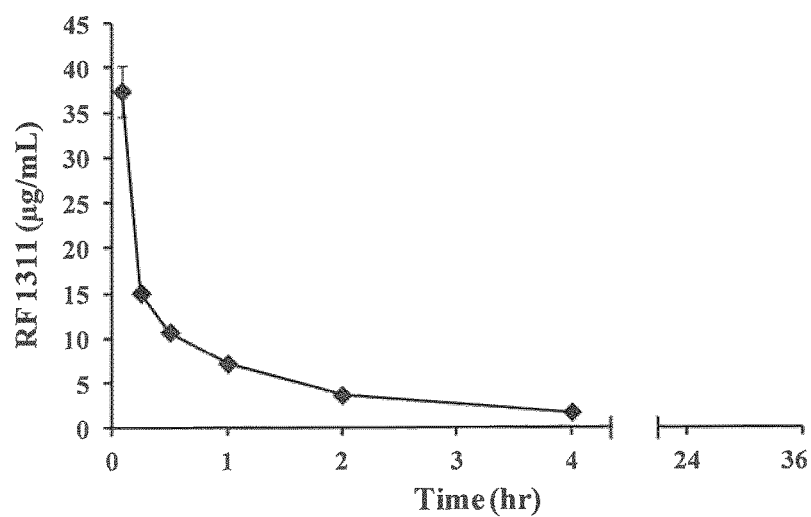
FIG. 5 is a graph illustrating the concentration of contrast agent RF1311 in plasma over time for rats intravenously administered with the contrast agent at a dose of 30 mg/kg.

Contrast agent RF1311 was prepared following the method outlined in Example 1 above. Rats were intravenously administered contrast agent RF1311 at a dose of 30 mg/kg. The plasma concentration of RF1311 was measured over time and is illustrated in FIG. 5. Each point is the mean+/−SE of the results from three different determinations.

No abnormal observations were noted following single dose intravenous administration of RF1311 at dose levels of 30 mg/kg. The half-life for elimination of RF1311 from rat plasma was 1.38 hr. At steady-state RF1311 had a distribution that was 1.54 fold the rat body weight.

The pharmacokinetic parameters for an intravenously administrated contrast agent RF1311 at in a single dose at 30 mg/kg are shown in Table 1, below.

TABLE 1

| Parameter | Units | Value |
| --- | --- | --- |
| $AUC_{0-tlast}$ | µg-hr/mL | 27.0 |
| $AUC_{0-\infty}$ | µg-hr/mL | 30.6 |
| $C_0$ | µg/mL | 58.8 |
| $C_{max}$ | µg/mL | 37.4 |
| $T_{max}$ | hr | 0.083 |
| $K_e$ | hr$^{-1}$ | 0.50 |
| $t_{1/2(e)}$ | hr | 1.38 |
| MRT | hr | 1.57 |
| Cl | L/hr/kg | 0.98 |
| Vz | L/kg | 1.96 |
| Vss | L/kg | 1.54 |

No abnormal observations were noted following the single doses of intravenously administered RF1311 at levels of 30, 60, 120 and 300 mg/kg. Based on the results of clinical observations, body weight and necropsy examinations, the maximum tolerated dose following a single intravenous administration was in excess of 300 mg/kg.

Example 12

Changes in Contrast Ratio Over Time Between Infarcted and Normal Tissues in RF1311 Treated Rats Over a 24 Hour Period Under Three Different MRI Conditions Rats weighing 300-400 grams were anesthetized with intraperitoneal injection of pentobarbital (Nembutal; Sanofi Sante Animale, Brussels, Belgium) at a dose of 40 mg/kg. Under laparotomy, reperfused partial liver infarction (RPLI) was induced by temporarily clamping the hilum of the right liver lobe for 3 hours. After reperfusion by declamping, the abdominal cavity was closed with two-layer sutures, and the rats were left to recover for 6 hours after the surgery, followed by MRI studies. Each rat was used as its own control for intra-individual comparison since both infarcted and normal liver tissues coexisted in the same animal.

Figure 6:
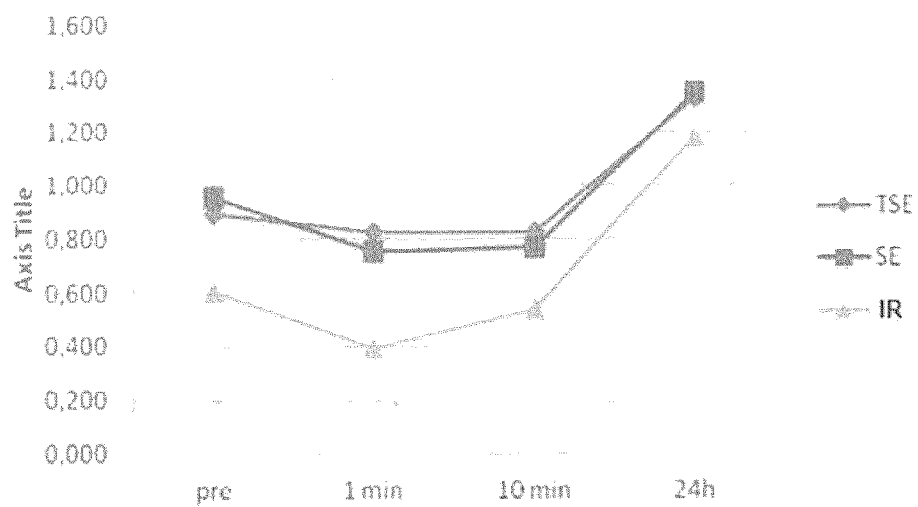
FIG. 6 is a graph illustrating the contrast ratio between infarcted and normal tissues in RF1311 treated rats over a 24 hour period under three different MRI conditions.

For the MRI studies, RF1311 was administered by single bolus injection via tail vein at a dose of 40 mg/kg. The contrast ratio was measured over a 24 hour period under three different MRI conditions: turbo spin-echo (TSE), spin echo (SE), and inversion recovery (IR). As can be seen from the results illustrated in FIG. 6, the contrast ratio after 24 hours is between 1.2 and 1.4, demonstrating the power of compound RF1311 to differentiate dead tissue over normal tissues.

Example 13

Myocardial Infarction

Myocardial infarction (MI) was induced in rabbits by open-chest coronary artery (CA) operation and close-chest CA reperfusion. Briefly, the procedure started with sedation or anesthesia, endotracheal intubation and mechanical ventilation, followed by the left 4-5th intercostal thoracotomy. After opening pericardium, the heart was slightly turned anticlockwise to expose the left circumflex (LCx) CA. A 2-0 silk suture was placed underneath the LCx at the level of 3 mm lower than the edge of the left atrial appendage and the MI was induced by tying the suture with a single knot with the detachable suture end from the knot left outside the thorax through the closed wound. Ninety minutes after CA occlusion, a reperfused MI was induced by pulling the exteriorized suture end in the closed-chest condition, which re-opened the detachable knot.

To further facilitate postmortem determination of the tissue components after myocardial ischemia, an approach with one stitch but two sutures was devised. Briefly, a sharp triangular needle of ½ circle with 2 spring eyes at the end (Sutura, Inc. Fountain Valley, Calif., USA) was used. Two silk sutures could be easily placed through the separate eyes: the thicker 2-0 suture was used for the CA ligation that could be removed for reperfusion and the thinner 5-0 one was spared for later ex vivo CA re-occlusion in order to perform postmortem multifunctional analysis.

Compound RF1311 was administered by bolus injection at 40 mg/kg over a 5 minute period. MRI images (in vivo and ex vivo) and photographs of heart tissues were obtained, as described below.

Figure 7A:
FIG. 7A is an MRI image of in vivo coronary artery tissue 24 hours after myocardial infarction was induced, where the tissue was treated with compound RF1311.
Figure 7B:
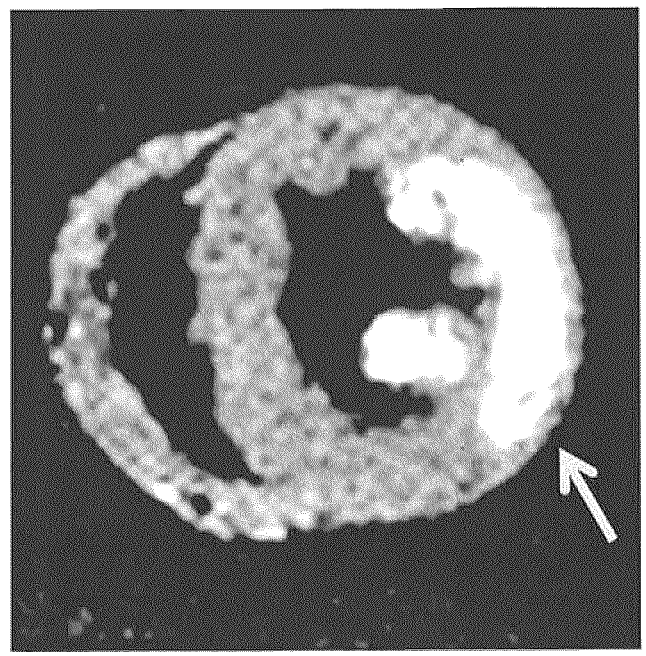
FIG. 7B is an MRI image of ex vivo coronary artery tissue, where the tissue corresponds to the tissue imaged in FIG. 7A.
Figure 7C:
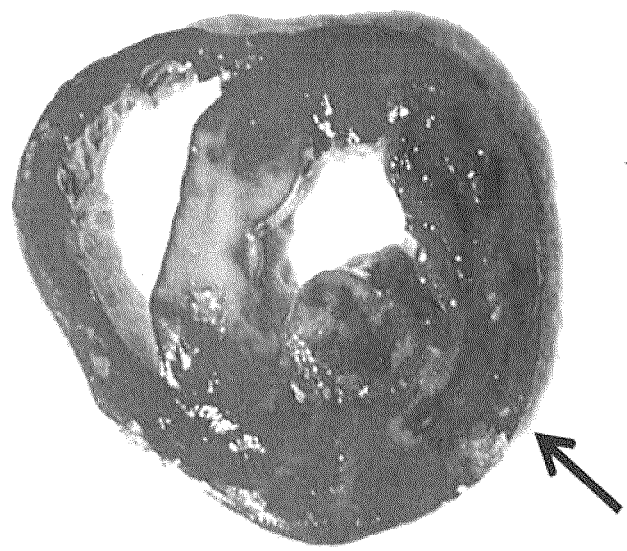
FIG. 7C a photograph of the tissue of FIG. 7B.
Figure 7D:
FIG. 7D is a photograph of the tissue of FIG. 7C which has been stained with triphenyltetrazolium chloride (TTC) to show necrotic tissue as a white area.

The results of the testing of compound RF1311 are shown in FIGS. 7A-7D. FIG. 7A is an MRI image showing a slice of a heart taken in vivo after 24 hours post injection with RF1311. The heart was removed and dissected to give a slice of cardiac tissue corresponding to the image in FIG. 7A. FIG. 7B is an MRI image of the cardiac tissue taken ex vivo. FIG. 7C is a photograph of the cardiac tissue used for the MRI of FIG. 7B. FIG. 7D is a photograph of the cardiac tissue used in FIGS. 7B and 7C, after the tissue was stained with triphenyltetrazolium chloride (TTC) to show necrotic tissue as a white area. The necrotic tissue is identified by the arrow, and the arrow in FIGS. 7A to 7C point to the same location. Although no clear cardiac damage can be seen in the unstained tissue shown in FIG. 7C, the necrotic tissue is stained by RF1311 as shown in FIGS. 7A and 7B.

The above-described embodiments are intended to be examples only. Alterations, modifications and variations can be effected to the particular embodiments by those of skill in the art without departing from the scope, which is defined solely by the claims appended hereto.

What is claimed is:

1. A contrast agent for administration to a subject, the contrast agent comprising:
   a targeting portion comprising a hydrazide functional group according to the formula:

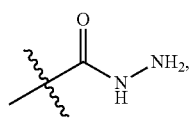 [SMILES: *C(=O)NN]

a metal ion bound to a metal-complexable portion, and a linker joining the targeting portion and the metal-complexable portion of the contrast agent wherein the contrast agent has the structure X-L-Y*M, wherein X is the targeting portion comprising the hydrazide functional group, L is the linker, and Y*M is the metal ion(M) bound to the metal-complexable portion (Y) of the contrast agent, wherein the contrast agent is:

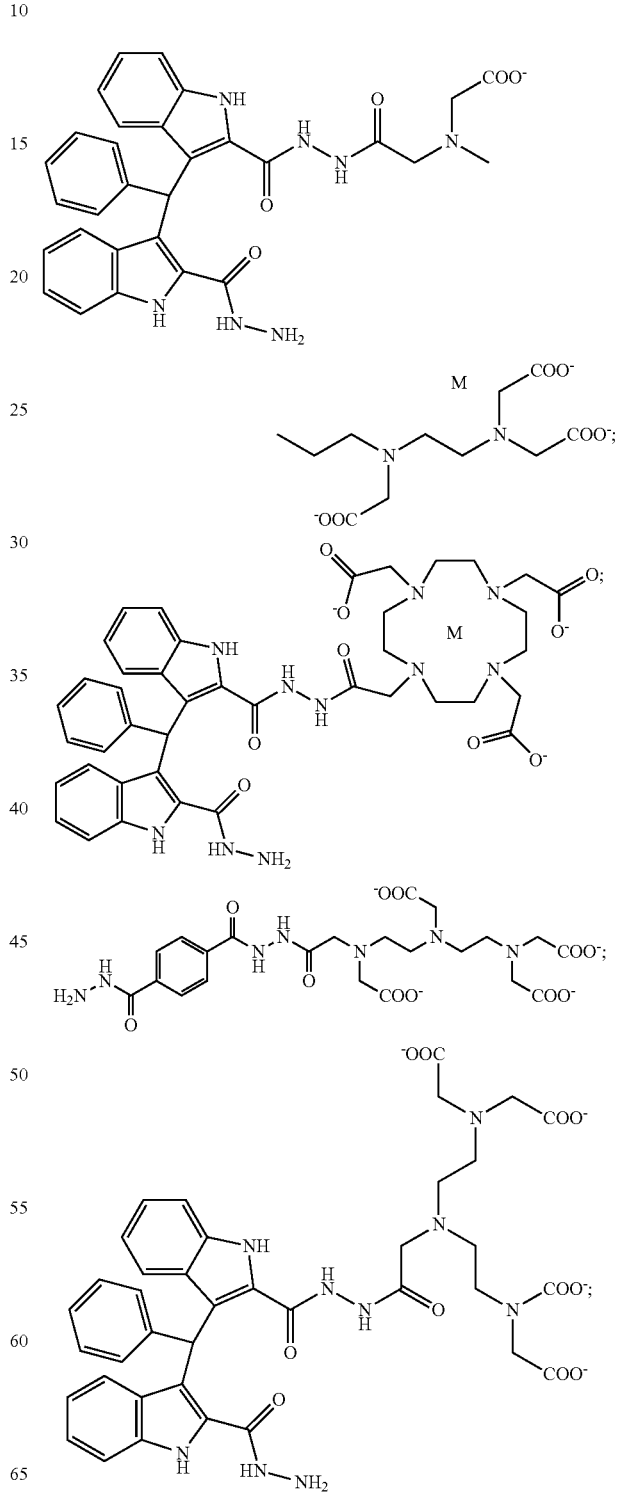

-continued

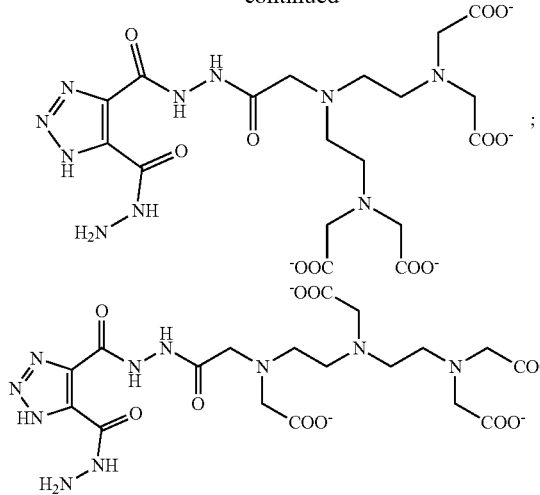

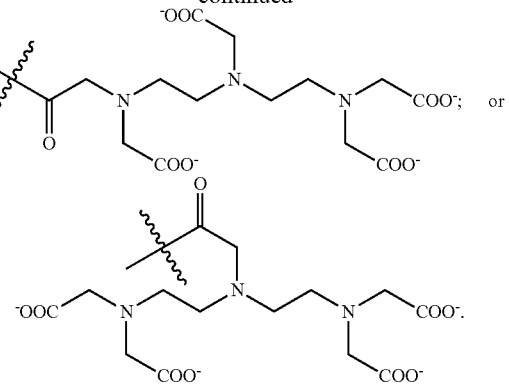

and the metal ion is selected from —Mn, Fe, Gd, $^{99m}$Tc, $^{111}$In, $^{64}$Cu, $^{90}$Y, $^{188}$Re, $^{186}$Re and $^{163}$Dy.

2. The contrast agent according to claim 1, wherein the metal-complexable portion of the contrast agent comprises an aminocarboxylate functional group.

3. The contrast agent according to claim 2, wherein the aminocarboxylate functional group is a polyaminocarboxylate functional group.

4. The contrast agent according to claim 2, wherein the aminocarboxylate functional group is:

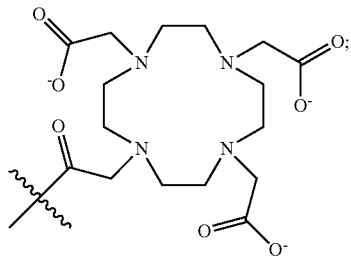

5. The contrast agent according to claim 1, wherein the linker is:

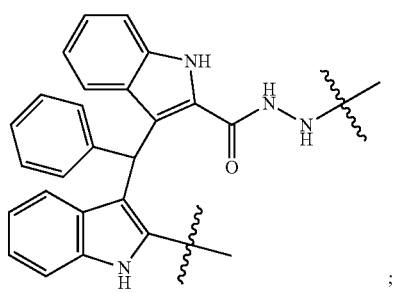

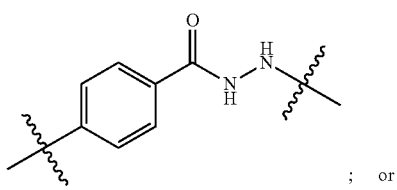

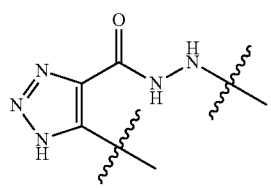

6. The contrast agent according to claim 1, wherein the metal ion is Gd$^{3+}$ and contrast agent is:

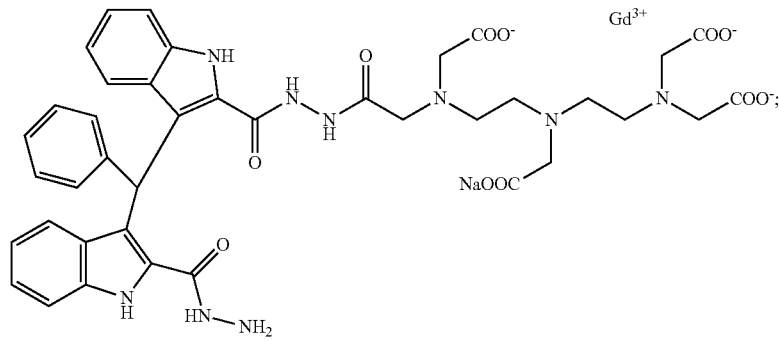

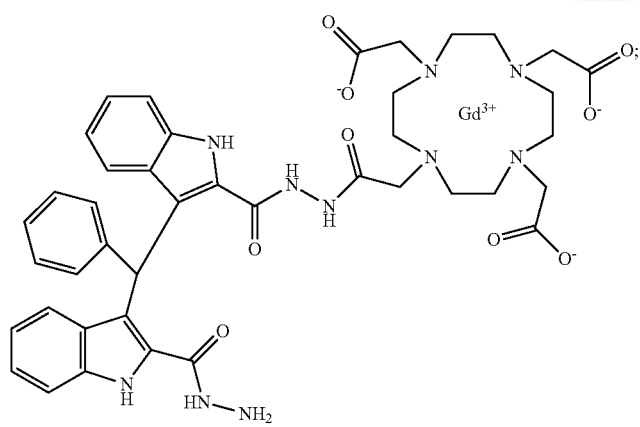
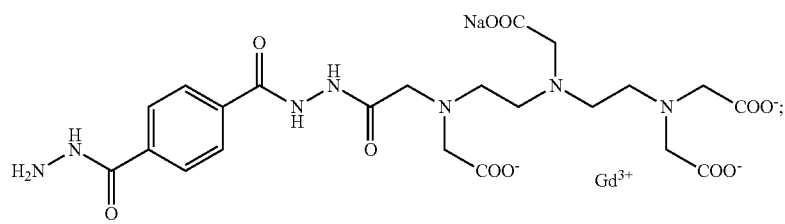
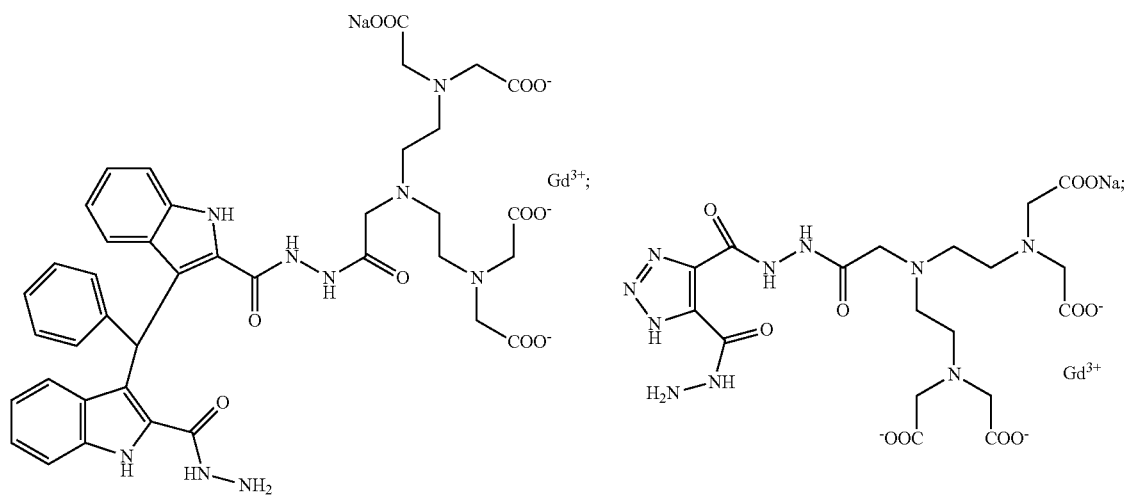
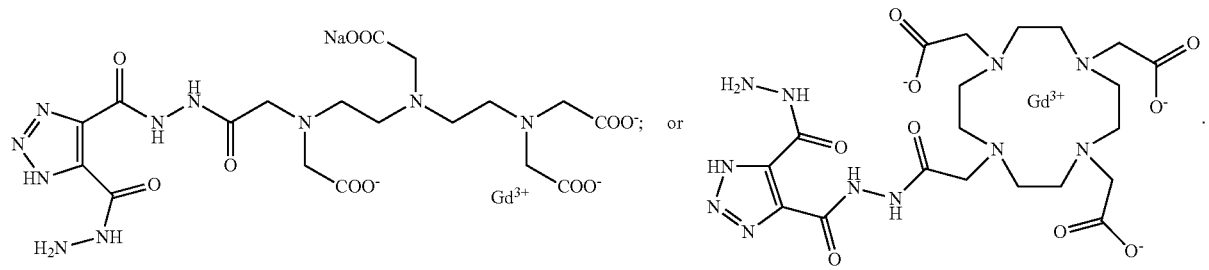

7. A composition comprising the contrast agent according to claim 1, and a pharmaceutically acceptable diluent or carrier.

8. A method comprising: administering a patient with a therapeutic dose or a diagnostic dose of the contrast agent according to claim 1, or the composition according to claim 7.

9. The method according to claim 8, wherein the method comprises administering a sufficient amount of the contrast agent to monitor the effectiveness of an ongoing therapeutic treatment.

10. A method comprising: administering a patient with a sufficient amount of the contrast agent according to claim 1 for the contrast agent to be visible in a diagnostic imaging or imaging-aided applications.

11. The method according to claim 10, wherein the diagnostic imaging or imaging-aided application is magnetic resonance imaging (MRI), computed tomography (CT), single-photon emission computed tomography (SPECT), positron emission tomography (PET), MRI-aided application, CT-aided application, SPECT-aided application, or PET-aided application.

\* \* \* \* \*